United States Patent
Kimmel et al.

(10) Patent No.: US 9,358,039 B2
(45) Date of Patent: Jun. 7, 2016

(54) TRANSSEPTAL NEEDLE APPARATUS

(71) Applicant: Greatbatch Ltd., Clarence, NY (US)

(72) Inventors: Scott Kimmel, St Paul, MN (US); Rodolphe Katra, Blaine, MN (US); Kevin Pietsch, Greenfield, MN (US); Brian Loushine, Maple Grove, MN (US); Jeffrey Zweber, St Louis Park, MN (US); Ed Goff, Mahtomedi, MN (US); Blane Larson, Maple Lake, MN (US); Jordon Honeck, Maple Grove, MN (US); Grant Scheibe, Loretto, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/888,845

(22) Filed: May 7, 2013

(65) Prior Publication Data
US 2013/0304036 A1 Nov. 14, 2013

Related U.S. Application Data
(60) Provisional application No. 61/644,180, filed on May 8, 2012.

(51) Int. Cl.
*A61B 17/34* (2006.01)
*A61B 18/14* (2006.01)
(Continued)

(52) U.S. Cl.
CPC ......... *A61B 17/3417* (2013.01); *A61B 17/3478* (2013.01); *A61B 17/3439* (2013.01);
(Continued)

(58) Field of Classification Search
CPC ............ A61M 25/01; A61M 25/0105; A61M 25/0113; A61M 25/06; A61M 25/0612; A61M 29/00; A61M 39/221; A61M 25/0606; A61M 25/0668; A61M 2025/0687; A61M 5/3202; A61M 5/50; A61M 39/1011; A61M 2019/304; A61M 2019/481; A61M 2025/0079; A61B 17/34; A61B 17/3415; A61B 17/3417; A61B 17/3421; A61B 17/3496; A61B 17/3439; A61B 18/18; A61B 2017/00247; A61B 2018/1425; A61B 218/007
USPC ........................... 604/264, 523, 528, 164.01, 604/164.06–164.09, 164.1, 164.11, 164.12, 604/167.01, 167.02
See application file for complete search history.

(56) References Cited

U.S. PATENT DOCUMENTS 4,483,338 A 11/1984 Bloom et al.
4,747,823 A * 5/1988 Buchanan ..................... 604/530
(Continued)

FOREIGN PATENT DOCUMENTS

DE 10004385 8/2001
EP 0455478 11/1991
(Continued)

OTHER PUBLICATIONS

Kimmel, Scott et al, "Transseptal Needle Apparatus Search Report".
(Continued)

*Primary Examiner* — Edelmira Bosques
*Assistant Examiner* — Nicholas Meghri
(74) *Attorney, Agent, or Firm* — Michael P. Horvath

(57) ABSTRACT

In various examples, an apparatus includes a needle assembly including an outer cannula including a tubular sidewall disposed around a lumen. At least a portion of the sidewall includes an exterior including a polymeric material configured to inhibit skiving of an interior of a dilator with movement of the outer cannula within the dilator. An inner cannula is disposed within the lumen and is selectively slidable with respect to the outer cannula. A handle is disposed at a proximal portion of the needle assembly. The handle includes a first handle portion coupled to and movable with the outer cannula. A second handle portion is coupled to and movable with the inner cannula, wherein the first handle portion is selectively movable with respect to the second handle portion to extend a distal end of the inner cannula from within the lumen of the outer cannula.

22 Claims, 20 Drawing Sheets

(51) Int. Cl.
    *A61B 18/18*      (2006.01)
    *A61B 17/00*      (2006.01)
    *A61B 19/00*      (2006.01)
    *A61M 39/10*      (2006.01)
    *A61M 25/00*      (2006.01)

(52) U.S. Cl.
    CPC ............. *A61B18/1477* (2013.01); *A61B 18/18* (2013.01); *A61B 2017/00247* (2013.01); *A61B 2018/1425* (2013.01); *A61B 2019/304* (2013.01); *A61B 2019/481* (2013.01); *A61B 2218/007* (2013.01); *A61M 39/1011* (2013.01); *A61M 2025/0079* (2013.01)

(56) References Cited

U.S. PATENT DOCUMENTS

| | | | |
|---|---|---|---|
| 5,429,616 | A | 7/1995 | Schaffer |
| 5,454,790 | A | 10/1995 | Dubrul |
| 5,487,728 | A * | 1/1996 | Vaillancourt .................. 604/86 |
| 5,578,052 | A | 11/1996 | Koros et al. |
| 5,782,807 | A | 7/1998 | Falvai et al. |
| 5,861,002 | A | 1/1999 | Desai |
| 6,063,081 | A | 5/2000 | Mulier et al. |
| 6,096,024 | A | 8/2000 | Graves et al. |
| 6,217,554 | B1 | 4/2001 | Green |
| 6,298,256 | B1 | 10/2001 | Meyer |
| 6,585,694 | B1 | 7/2003 | Smith et al. |
| 6,723,082 | B1 | 4/2004 | Payne et al. |
| 7,001,396 | B2 | 2/2006 | Glazier et al. |
| 8,016,784 | B1 | 9/2011 | Hayzelden et al. |
| 2001/0014806 | A1 | 8/2001 | Ellman et al. |
| 2002/0010416 | A1 * | 1/2002 | Uflacker ........................ 604/35 |
| 2002/0143291 | A1 | 10/2002 | Slater et al. |
| 2002/0183738 | A1 | 12/2002 | Chee et al. |
| 2003/0100862 | A1 * | 5/2003 | Edwards et al. ............. 604/138 |
| 2003/0187460 | A1 | 10/2003 | Chin et al. |
| 2004/0143262 | A1 | 7/2004 | Visram et al. |
| 2004/0147877 | A1 * | 7/2004 | Heuser .................... 604/165.02 |
| 2005/0149097 | A1 | 7/2005 | Regnell et al. |
| 2005/0277889 | A1 | 12/2005 | Neidert et al. |
| 2006/0155246 | A1 | 7/2006 | Higuchi et al. |
| 2007/0005019 | A1 | 1/2007 | Okishige |
| 2007/0270751 | A1* | 11/2007 | Stangenes et al. ......... 604/164.1 |
| 2008/0161792 | A1 | 7/2008 | Wang et al. |
| 2008/0262318 | A1 | 10/2008 | Gorek et al. |
| 2008/0262430 | A1 | 10/2008 | Anderson et al. |
| 2009/0062784 | A1 | 3/2009 | Kobayashi et al. |
| 2009/0062795 | A1 | 3/2009 | Vakharia et al. |
| 2009/0105742 | A1 | 4/2009 | Kurth et al. |
| 2009/0171276 | A1 | 7/2009 | Bednarek et al. |
| 2010/0204696 | A1 | 8/2010 | Mathonnet |
| 2011/0160538 | A1 | 6/2011 | Ravikumar et al. |

FOREIGN PATENT DOCUMENTS

| | | |
|---|---|---|
| EP | 0537573 | 4/1993 |
| EP | 1462141 | 9/2004 |
| EP | 1683543 | 7/2006 |
| EP | 1736108 | 12/2006 |
| EP | 1857135 | 11/2007 |
| WO | 00/56238 | 9/2000 |
| WO | 02/32335 | 4/2002 |
| WO | 03077982 | 9/2003 |
| WO | 2005018732 | 3/2005 |
| WO | 2005104973 B | 11/2005 |
| WO | 2006/138462 | 12/2006 |
| WO | 2010/088239 B | 8/2010 |
| WO | 2012/125239 | 9/2012 |

OTHER PUBLICATIONS

Ross J., Jr.: Transseptal left heart catheterization a 50-year odyssey. Journal of the American College of Cardiology. 2008; 51: 2107-2115. Doi: 10.1016/j.jacc.2007.12.060.

Cope, C.: Newer Techniques of Transseptal Left-Heart Catheterization. Circulation Journal of the American Heart Association. 1963; 27: 758-761. Doi: 10.1161/01.Cir.27.4.758.

Feld GK, Tiongson J, Oshodi G.: Particle formation and risk of embolization during transseptal catheterization: comparison of standard transseptal needles and a new radiofrequency transseptal needle. J Intent Card Electrophsiol. Jan. 2011; 30(1): 31-6.

Sangiorgi G, Colombo A.; Embolic protection devices: Heart. Sep. 2003; 89(9): 990-992.

EP Search dated May 7, 2014 for EP Application No. 13167149.7.

Communication pursuant to Article 94(3) EPC, Four month Office Action in Application 13167145.5, dated Nov. 5, 2015.

\* cited by examiner

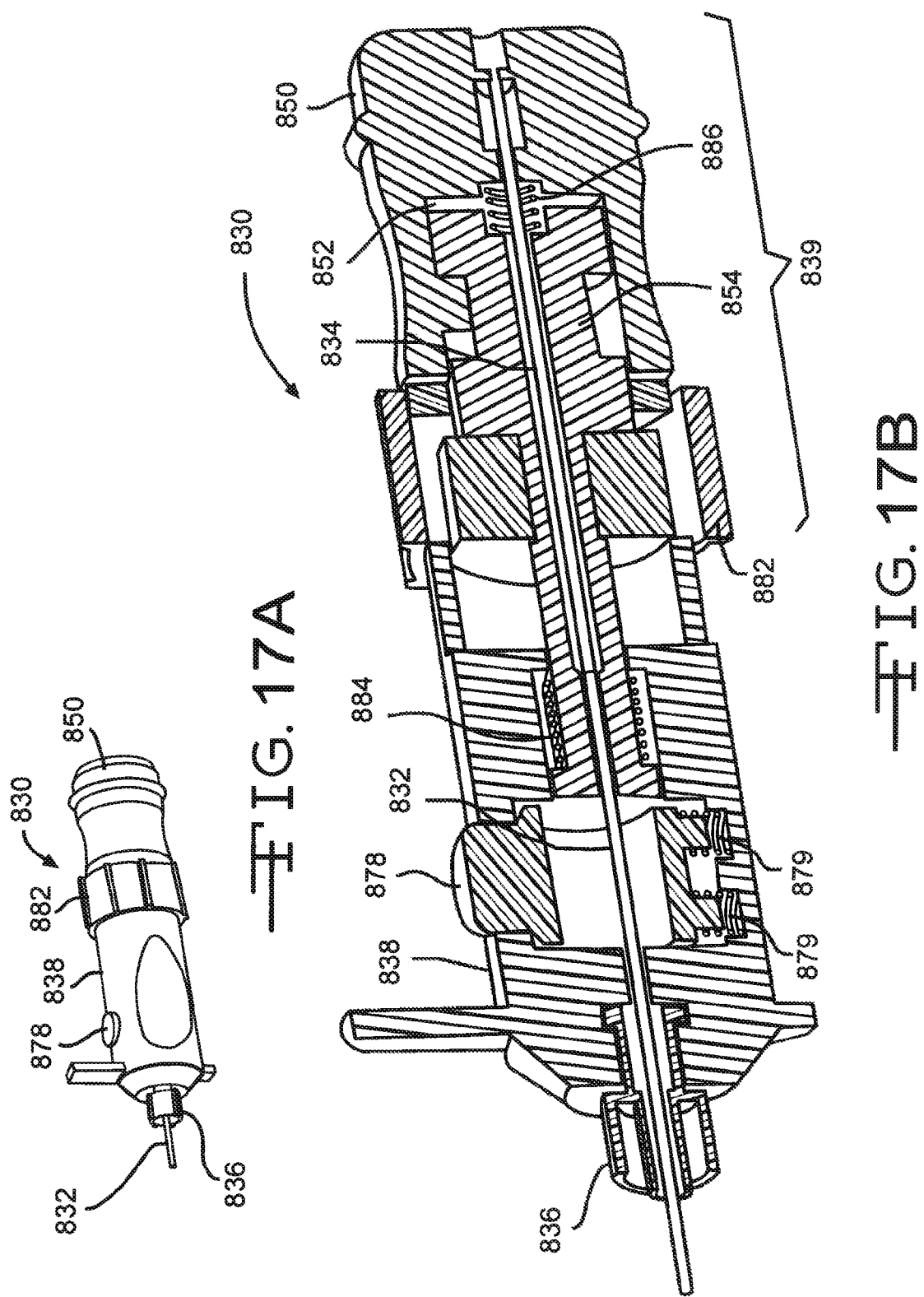

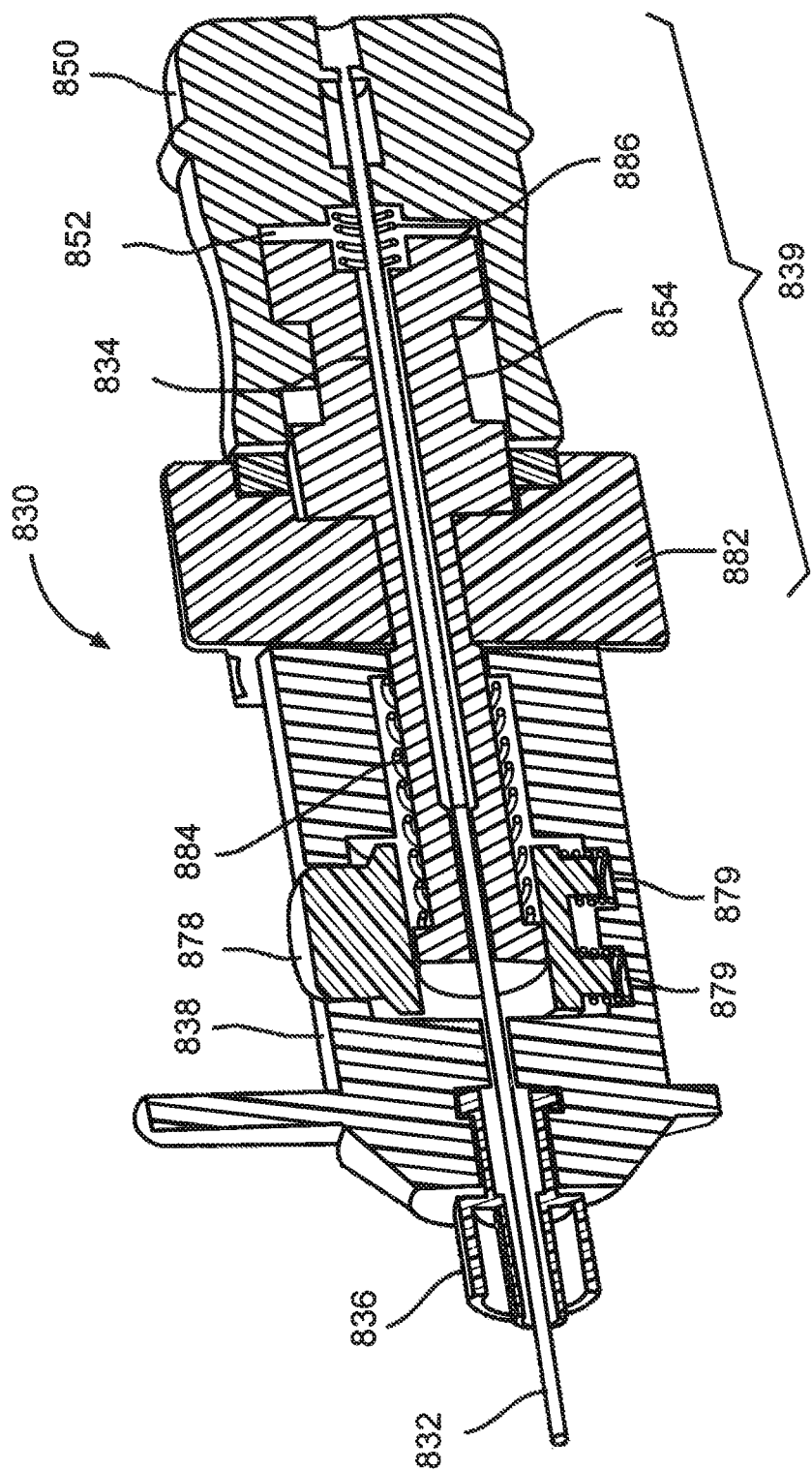

TRANSSEPTAL NEEDLE APPARATUS

CROSS REFERENCE TO RELATED APPLICATIONS

This application claims the benefit of priority to U.S. Provisional Application Ser. No. 61/644,180, filed on May 8, 2012, entitled "TRANSSEPTAL NEEDLE," which is incorporated by reference herein in its entirety.

BACKGROUND

The present invention relates to transseptal catheterization, and more specifically relates to a needle assembly for transseptal catheterization.

The human heart contains four chambers: the right atrium, the right ventricle, the left atrium, and the left ventricle. The right atrium is in fluid contact with the superior vena cava (SVC) and the inferior vena cava (IVC). The right atrium is separated from the right ventricle by the tricuspid valve, while the left atrium is separated from the left ventricle by the mitral valve. The right atrium and left atrium are separated by the interatrial septum, while the right ventricle and left ventricle are separated by the interventricular septum.

There are a multitude of therapeutic and diagnostic procedures in which a catheter is passed within a guide sheath or over a guide wire to access the chambers of the heart. The right atrium can be accessed from the superior vena cava or inferior vena cava. The right ventricle can be accessed from the right atrium. The left ventricle can be accessed from the aorta. The left atrium can be accessed directly from the left ventricle (through the mitral valve); however, such an approach is a relatively difficult maneuver due in part to the tortuous path that must be navigated with the catheter. Such a maneuver is problematic for various reasons, including a bleeding risk and a clotting risk to the patient (because it is the arterial side, it has a relatively high pressure, which exacerbates such risks). In addition, this approach may cause arrhythmias. Therefore, another approach for accessing the left atrium was developed. In this approach, a small hole is placed in the interatrial septum, so that the left atrium can be accessed from the right atrium. This hole is typically created by a needle puncture and is referred to as transseptal catheterization.

In the standard transseptal catheterization procedure, three main, separate tools are involved: a sheath with a sheath hub, a dilator with a dilator hub, and a needle assembly including a cannula, a needle hub and a stylet. The stylet is usually a small, guidewire-like device that is threaded through the needle cannula and attaches to the needle hub proximally. The distal tip of the stylet extends beyond the distal tip of the needle. The distal section of the needle has a shoulder or tapered section that corresponds with an internal taper at the distal tip of the dilator. When the needle is fully inserted into the dilator, the needle shoulder functions as a hard stop that limits the distance that the tip of the needle can exit from the dilator.

The typical transseptal procedure entails numerous steps. First, right femoral vein access is gained via the Seldinger technique. Second, a guidewire is passed through an introducer sheath, which was placed in the first step, into the femoral vein and threaded up the IVC to the SVC. Third, a sheath and dilator assembly is maneuvered to the SVC by being passed over the guidewire. Fourth, the guidewire is removed. Fifth, the needle assembly, usually including a stylet, is advanced through the inner lumen of the dilator until the distal tip of the needle (or stylet) is just proximal of the distal tip of the dilator. Sixth, the stylet, if present, is removed, and the needle is advanced until the tip of the needle is just proximal of the distal tip of the dilator. Seventh, the dilator/sheath/needle assembly is pulled caudally until the distal tip of the dilator is just resting on the fossa ovalis, which is a relatively thin area in the interatrial septum. Eighth, the needle is advanced forward through the dilator to puncture the septal wall (fossa ovalis). Ninth, and finally, the sheath and dilator assembly is fed through the septal wall over the needle, thereby gaining access to the left atrium.

One risk associated with transseptal needle use is inadvertent exposure. The sheath/dilator assembly and transseptal needle assembly are usually not interlocking Thus, the needle assembly can freely translate and rotate within the sheath/dilator assembly. This freedom of movement means that the position of the needle assembly in relation to the sheath/dilator assembly must be manually maintained by the user. In particular, during the needle insertion step and the subsequent navigation of the tip of the sheath/dilator/needle assembly to the fossa ovalis, if the translational position of the needle assembly is not controlled or monitored, there is a risk of inadvertent exposure of the stylet and/or needle tip The maintenance of needle position in relation to the dilator is especially challenging for inexperienced users. Inadvertent exposure can result in damage to the vascular and cardiac walls, which could further result in generation of potentially dangerous emboli.

In the standard transseptal procedure, in order to mitigate this risk, the physician performs a measurement ex vivo to determine the point at which the stylet and/or needle tip is unexposed and just proximal of the dilator tip. To do this, the physician first inserts the needle fully into the dilator so that the stylet and/or needle tip exits the dilator. Next, the physician withdraws the needle proximally so that the stylet and/or needle tip is no longer exposed. At this point, the physician measures how far the needle handle is proximally offset from the dilator hub. Generally, this offset distance is "two-finger-widths" if the stylet is connected to the needle and "one-finger-width" if the stylet has been removed. This is an imprecise and non-standardized measurement that adds an extra step to the procedure. In addition, when the needle is inserted into the dilator/sheath assembly, which has been placed previously in vivo and in the SVC, the physician has to take care so that the needle does not advance beyond the offset distance(s) that had been previously measured.

A second risk is the inadvertent puncture of adjacent structures rather than the fossa ovalis. These adjacent structures include: the aortic root, the coronary sinus, and the posterior free wall of the right atrium. If perforation is limited to just the needle, the result is usually benign. However, if the dilator/sheath assembly is advanced over the needle into the aortic root or pericardium, complications, such as cardiac tamponade, can occur.

In the standard transseptal procedure, in order to mitigate this risk, the physician uses adjunctive techniques and technology to locate the transseptal tools relative to the pertinent intracardiac structures, especially the fossa ovalis. These adjunctive techniques and technology comprise one or any combination of the following: biplane fluoroscopy; use of a pig-tailed catheter to identify the aortic root; pressure manometry to identify aortic/right atrial and left atrial pressures; contrast infusion; and transesophageal (TEE) and intracardiac (ICE) echocardiography.

A third risk is the generation of particulates as the needle is advanced through the dilator. During this needle advancement, the tip of the needle has the potential to skive the inner surface of the dilator, especially at the tapered tip section.

Since the needle and dilator are advanced into the left atrium, one of these particulates could be released and travel from the left atrium directly to the carotid or coronary arteries. The particulate could then, if large enough, block one of the arteries, resulting in a stroke or myocardial infarction. In the standard transseptal procedure, in order to mitigate this risk, the needle and dilator assembly are flushed after the ex vivo measurement step. In addition, the purpose of the stylet, which is re-attached to the needle after the flushing step, is to act as a guidewire and prevent the tip of the needle from skiving the dilator inner surface during needle advancement through the dilator.

A fourth risk is the generation of air emboli during the puncture procedure. There is no seal between the needle cannula and the dilator hub at the proximal end of the needle/dilator/sheath assembly. This creates a potential path for air to travel into the patient's heart, which can result in the formation of an air embolism. This is particularly risky if the air exits the distal tip of the dilator while it is in the left atrium; an air embolism in the left atrium can travel directly to the brain and cause a cerebral ischemic event.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that the subject matter can be used to decrease the likelihood that a needle assembly will produce particulate matter, for instance, during insertion of the needle assembly into a dilator. The present subject matter can also be used to decrease the risk of inadvertent exposure of the inner cannula tip. To better illustrate the apparatuses and methods described herein, a non-limiting list of examples is provided here:

Example 1 can include subject matter that can include an apparatus including a needle assembly including an outer cannula including a tubular sidewall disposed around a lumen. At least a portion of the sidewall includes an exterior including a polymeric material configured to inhibit skiving of an interior of a dilator with movement of the outer cannula within the dilator. An inner cannula is disposed within the lumen and is selectively slidable with respect to the outer cannula. A handle is disposed at a proximal portion of the needle assembly. The handle includes a first handle portion coupled to and movable with the outer cannula. A second handle portion is coupled to and movable with the inner cannula, wherein the first handle portion is selectively movable with respect to the second handle portion to extend a distal end of the inner cannula from within the lumen of the outer cannula.

In Example 2, the subject matter of Example 1 is optionally configured such that the outer cannula is formed from the polymeric material.

In Example 3, the subject matter of any one of Examples 1-2 is optionally configured such that the outer cannula is formed from polyethylene.

In Example 4, the subject matter of Example 3 is optionally configured such that the outer cannula is formed from Petrothane.

In Example 5, the subject matter of any one of Examples 1-4 optionally includes a handle lock including a first position in which the handle lock inhibits movement of the second handle portion with respect to the first handle portion and a second position in which the handle lock allows movement of the second handle portion with respect to the first handle portion.

In Example 6, the subject matter of Example 5 is optionally configured such that the handle lock includes a spacer removably disposed with respect to the handle. The spacer in the first position includes the spacer engaged with the handle to inhibit movement of the second handle portion with respect to the first handle portion. The spacer in the second position includes the spacer removed from engagement with the handle to allow movement of the second handle portion with respect to the first handle portion to allow movement of the inner cannula with respect to the outer cannula.

In Example 7, the subject matter of any one of Examples 5-6 is optionally configured such that the handle lock includes a movable lock associated with the handle. The movable lock in the first position includes the movable lock disposed with respect to the handle to inhibit movement of the second handle portion with respect to the first handle portion. The movable lock in the second position includes the movable lock disposed with respect to the handle to allow movement of the second handle portion with respect to the first handle portion to allow movement of the inner cannula with respect to the outer cannula.

In Example 8, the subject matter of Example 7 is optionally configured such that the movable lock includes a rotational lock, wherein the rotational lock in the first position includes the rotational lock in a first rotational orientation with respect to the handle, and the rotational lock in the second position includes the rotational lock in a second rotational orientation with respect to the handle.

In Example 9, the subject matter of Example 8 is optionally configured such that one of the rotational lock and the handle includes a protrusion and the other of the rotational lock and the handle includes a slot, wherein in the first rotational orientation, the slot and the protrusion are misaligned to inhibit movement of the second handle portion with respect to the first handle portion, and, in the second rotational orientation, the slot and the protrusion are aligned to allow the protrusion to move within the slot and allow movement of the second handle portion with respect to the first handle portion.

In Example 10, the subject matter of any one of Examples 1-9 optionally includes a puncture assembly including a potential energy storage member disposed between the first handle portion and the second handle portion. An actuator is operatively coupled to the potential energy storage member, wherein triggering of the actuator releases the potential energy storage member to move the second handle portion with respect to the first handle portion.

In Example 11, the subject matter of Example 10 is optionally configured such that the potential energy storage member includes a spring.

In Example 12, the subject matter of any one of Examples 10-11 optionally includes a guard movable between a locked position and an unlocked position, wherein the guard in the locked position inhibits releasing of the potential energy storage member, and the guard in the unlocked position allows releasing of the potential energy storage member.

In Example 13, the subject matter of Example 12 is optionally configured such that the guard in the locked position covers the actuator, and the guard in the unlocked position allows access to the actuator.

In Example 14, the subject matter of any one of Examples 1-13 optionally includes an adjustable stop associated with the handle, wherein movement of the adjustable stop adjusts a distance the first handle portion is movable with respect to the second handle portion to adjust a puncture length of the inner cannula. The puncture length includes a distance the distal end of the inner cannula extends from within the lumen of the outer cannula with movement of the first handle portion with respect to the second handle portion.

In Example 15, the subject matter of any one of Examples 1-14 optionally includes an outer cannula cover which covers over a distal opening of the outer cannula. The outer cannula cover is puncturable by the inner cannula with extension of the distal end of the inner cannula from within the lumen and out of the distal opening of the outer cannula.

In Example 16, the subject matter of any one of Examples 1-15 is optionally configured such that the distal end of the inner cannula is biased to a position within the lumen of the outer cannula, such that the distal end of the inner cannula withdraws back into the outer cannula after a puncture is performed.

Example 17 can include, or can optionally be combined with any one of Examples 1-16 to include subject matter that can include an apparatus including a needle assembly including an outer cannula including a tubular sidewall disposed around a lumen. At least a portion of the sidewall includes an exterior including a polymeric material configured to inhibit skiving of an interior of a dilator with movement of the outer cannula within the dilator. An inner cannula is disposed within the lumen and selectively slidable with respect to the outer cannula. A handle is disposed at a proximal portion of the needle assembly. The handle includes a first handle portion coupled to and movable with the outer cannula. A second handle portion is coupled to and movable with the inner cannula, wherein the first handle portion is selectively movable with respect to the second handle portion to extend a distal end of the inner cannula from within the lumen of the outer cannula. A handle lock includes a first position in which the handle lock inhibits movement of the second handle portion with respect to the first handle portion and a second position in which the handle lock allows movement of the second handle portion with respect to the first handle portion.

In Example 18, the subject matter of Example 17 is optionally configured such that the outer cannula is formed entirely from the polymeric material.

In Example 19, the subject matter of any one of Examples 17-18 is optionally configured such that the handle lock includes a spacer removably disposed with respect to the handle, wherein the spacer in the first position includes the spacer engaged with the handle to inhibit movement of the second handle portion with respect to the first handle portion, and the spacer in the second position includes the spacer removed from engagement with the handle to allow movement of the second handle portion with respect to the first handle portion to allow movement of the inner cannula with respect to the outer cannula.

In Example 20, the subject matter of any one of Examples 17-19 optionally includes a puncture assembly including a potential energy storage member disposed between the first handle portion and the second handle portion. An actuator is operatively coupled to the potential energy storage member, wherein triggering of the actuator releases the potential energy storage member to move the second handle portion with respect to the first handle portion.

BRIEF DESCRIPTION OF THE DRAWINGS

FIG. 17A is a perspective view of a needle assembly in accordance with at least one example of the invention.

FIG. 17B is a cross-sectional view of the needle assembly of FIG. 17A.

FIGS. 18A-18F are cross-sectional views of a needle assembly in accordance with at least one example of the invention.

DETAILED DESCRIPTION

The present patent application relates to apparatuses and methods related to a needle assembly. The apparatuses and methods, in some examples, are used in various procedures, including, but not limited to, tissue puncture procedures, interatrial septum puncture procedures, or transseptal catheterization procedures.

The present subject matter provides a needle assembly for transseptal catheterization, in some examples, that lessens the likelihood that the needle assembly will produce particulate matter, for instance, during insertion of the needle assembly into a dilator. That is, the needle assembly, in some examples, inhibits production of particulate matter, for instance, from skiving or otherwise scraping an inside of a dilator with a needle tip. In various examples, the needle assembly of the present subject matter also lessens the need for a stylet and allows a tip of an inner cannula to be sharper than most conventional transseptal needles, since the tip of the inner cannula remains housed within the outer cannula until a physician or other user is ready to perform a puncture. Additionally, the sharper tip of the inner cannula, in some examples, can allow the physician or other user to puncture an aneurismal septum or a fibrotic septum where a conventional transseptal needle would be ineffective to puncture such an aneurismal septum or fibrotic septum. The example needle assemblies of the present subject matter additionally can decrease the risk of inadvertent exposure of the inner cannula tip, as well as decrease the need for ex vivo measurement steps typically performed to guard against inadvertent exposure. In various examples, the needle assembly of the present subject matter also decreases the likelihood of air emboli generation that can occur during puncture of a tissue layer.

Figure 1:
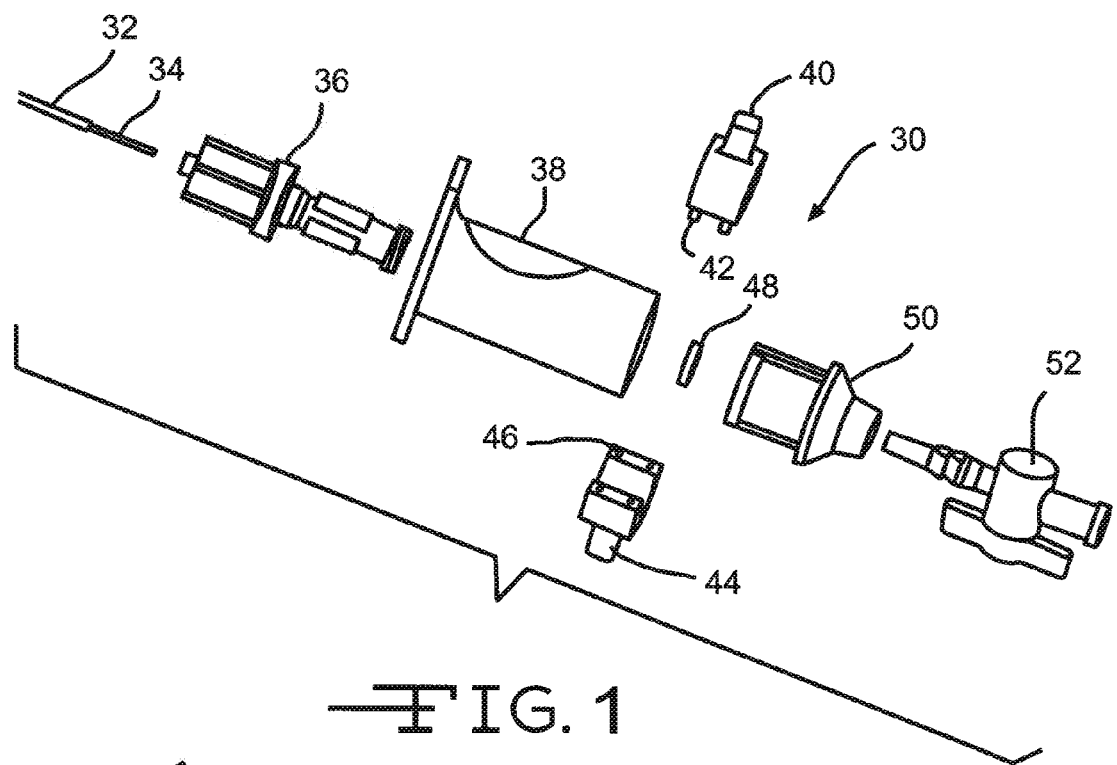
FIG. 1 is an exploded view of a needle assembly in accordance with at least one example of the invention.

Referring to FIG. 1, in some examples, a transseptal needle assembly 30 includes an outer cannula 32, an inner cannula 34, a rotating Luer fitting 36, a distal handle 38, a spacer top 40, one or more pins 42, a spacer bottom 44, one or more pin holes 46, a hemostatic valve 48, a proximal handle 50, and a stopcock 52 or other coupling assembly. The outer cannula 32, in some examples, is connected to the distal handle 38. In some examples, the inner cannula 34 is connected to the proximal handle 50. In some examples, the inner cannula 34 is slidable within the outer cannula 32. In some examples, the proximal handle 50 fits into or otherwise on the distal handle 38 and is slidable with respect to the distal handle 38. The spacer top 40 and spacer bottom 44, in some examples, can form a removable spacer selectively held together, for instance, by a compression fit of the one or more pins 42 into the one or more pin holes 46. In some examples, when the spacer top 40 and the spacer bottom 44 are removed, the proximal handle 50 is slidable forward with respect to the distal handle 38, allowing the inner cannula 34 to slide forward within the outer cannula 32. In some examples, the stopcock 52 or other coupling assembly connects to the proximal handle 50 and is fluidly continuous with the inner cannula 34. The stopcock 52 or other coupling assembly, in some examples, is connectable to tools that may be used during transseptal catheterization, such as a syringe with contrast material, for instance, which can be used to allow a physician or other user to determine the position of the outer cannula 32 or the inner cannula 34 within a patient.

Figure 2:
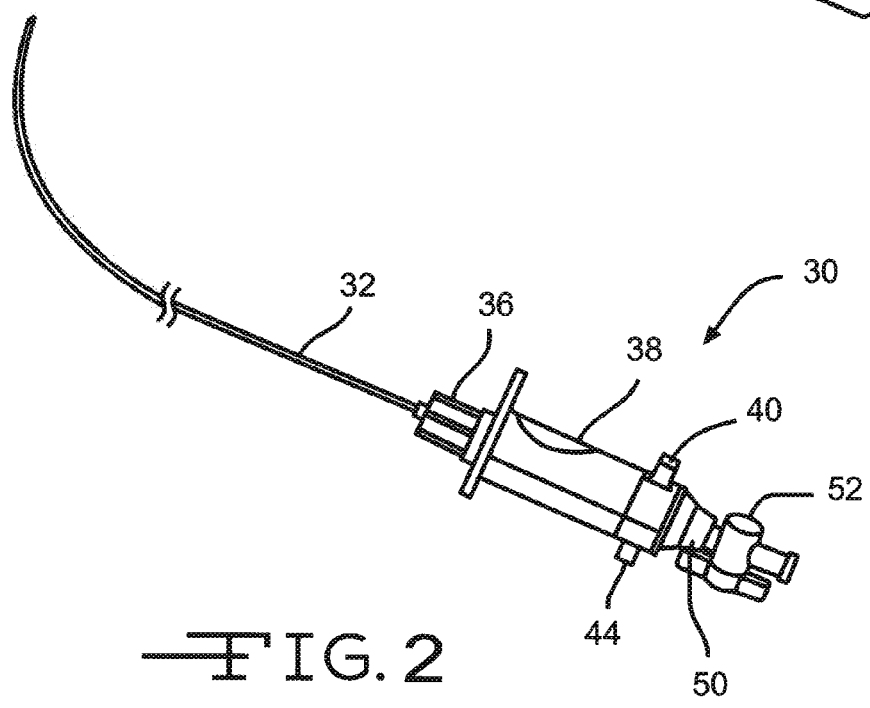
FIG. 2 is a perspective view of a needle assembly in accordance with at least one example of the invention.

Referring to FIG. 2, in some examples, the transseptal needle assembly 30 includes the outer cannula 32 disposed within or through the rotating Luer fitting 36. In some examples, the rotating Luer fitting 36 is connected to the distal handle 38. In some examples, the rotating Luer fitting 36 is fixed to the distal handle 38.

Referring to FIGS. 1 and 2, in some examples, once a sheath and a dilator are in place within the patient to begin a transseptal catheterization, the physician or other user can insert the outer cannula 32 completely within the dilator and attach the rotating Luer fitting 36 to a dilator hub. The proximal handle 50, in some examples, is kept from sliding forward within the distal handle 38 by the compression fit of the spacer top 40 and the spacer bottom 44. This decreases the likelihood of the inner cannula 34 extending from the outer cannula 32 unexpectedly and inadvertently exposing the patient to the inner cannula 34. In some examples, this lessens, if not eliminates, the need to perform ex vivo measurement steps to mitigate inadvertent exposure.

In some examples, the attachment of the rotating Luer fitting 36 to the dilator hub creates a seal between the outer cannula 32 and the dilator hub, limiting, if not eliminating, a potential path for air to travel into the patient's heart, thereby limiting, if not eliminating the possibility of the formation of an air embolism within the patient during a procedure. Once this seal is created, in some examples, the physician or other user may aspirate the transseptal needle assembly 30 to remove air that could generate air emboli. The rotating Luer fitting 36, in some examples, may connect the distal handle 38 to the dilator hub such that the rotating Luer fitting 36 inhibits translational motion of the distal handle 38. In some examples, the rotating Luer fitting 36 allows rotational motion of the distal handle 38 so that the transseptal needle assembly 30 may be properly oriented within the patient's heart, for instance, for puncture of the fossa ovalis.

In some examples, once the physician or other user properly orients the transseptal needle assembly 30, the physician or other user may remove the spacer top 40 and the spacer bottom 44 to allow translational motion of the proximal handle 50 with respect to the distal handle 38. The physician or other user, in some examples, may then slide the proximal handle 50 forward with respect to the distal handle 38, causing a tip of the inner cannula 34 to exit the outer cannula 32 and the dilator and puncture a tissue layer, such as, for instance, the patient's fossa ovalis. The physician or other user, in some examples, can then confirm that the inner cannula 34 is in the left atrium by performing a contrast injection using a syringe attached to the stopcock 52 or other coupling assembly. In some examples, the physician or other user can hold onto the proximal handle 50 while pushing the distal handle 38 forward, which pushes the dilator and the sheath over the inner cannula 34 and, for instance, into the patient's left atrium.

Figure 3:
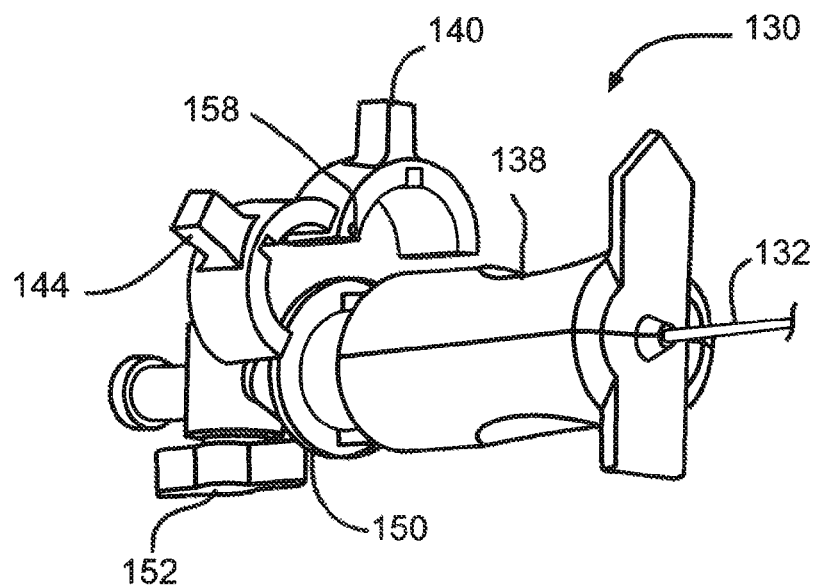
FIG. 3 is a perspective view of a needle assembly in accordance with at least one example of the invention.

Referring to FIG. 3, in some examples, a transseptal needle assembly 130 includes a spacer including a hinge 158 coupling a spacer top 140 and a spacer bottom 144. The transseptal needle assembly 130, in some examples, includes an outer cannula 132, a distal handle 138, the spacer top 140, the spacer bottom 144, a proximal handle 150, a stopcock 152 or other coupling assembly, and the hinge 158. In some examples, the spacer top 140 and the spacer bottom 144 can form a removable spacer held together by the hinge 158. In some examples, when the hinge 158 is released, the spacer top 140 and the spacer bottom 144 can be removed from the transseptal needle assembly 130, allowing slidable movement of the proximal handle 150 with respect to the distal handle 138.

Figure 4:
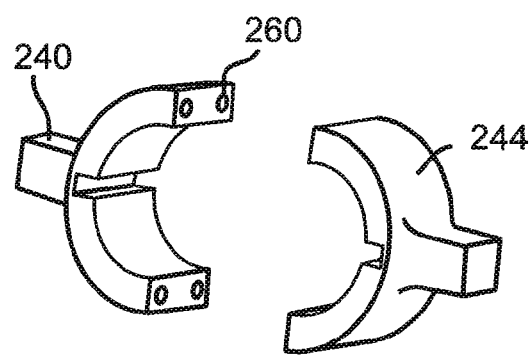
FIG. 4 is a perspective view of an example of a spacer for a needle assembly in accordance with at least one example of the invention.

Referring to FIG. 4, in some examples, a spacer top 240 and a spacer bottom 244 are selectively coupled using a spacer connection 260. The spacer top 240 and the spacer bottom 244, in some examples, can form a removable spacer held together by the spacer connection 260. In some examples, the spacer connection 260 can magnetically hold together the spacer top 240 and the spacer bottom 244. In some examples, the magnetic connection can be broken by the physician or other user, and the spacer top 240 and the spacer bottom 244 can be selectively removed from the transseptal needle assembly 130. In various examples, the spacer top 240 and the spacer bottom 244 can be selectively held together using another connection feature, such as, but not limited to adhesive, a tab-in-slot connection, or the like. In some examples, the spacer connection 260 can include adhesive configured to hold together the spacer top 240 and the spacer bottom 244. In some examples, the adhesive connection can be broken and the spacer top 240 and the spacer bottom 244 can be selectively removed from the transseptal needle assembly 130.

Figure 5:
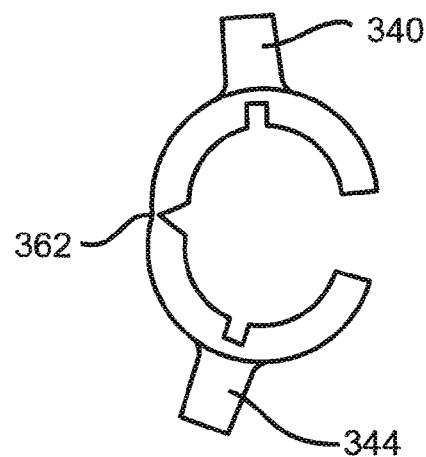
FIG. 5 is a front view of an example of a spacer for a needle assembly in accordance with at least one example of the invention.

In some examples, referring to FIG. 5, a living hinge 362 can be used to connect a spacer top 340 and a spacer bottom 344. The spacer top 340 and the spacer bottom 344, in some examples, can form a removable spacer held together by the living hinge 362. In some examples, when the living hinge 362 is released, the spacer top 340 and the spacer bottom 344 can be removed from a transseptal needle assembly.

Figure 6A:
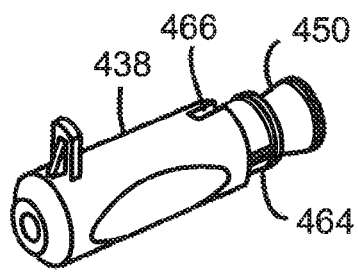
FIGS. 6A-6C are perspective views of a needle assembly in accordance with at least one example of the invention.
Figure 6B:
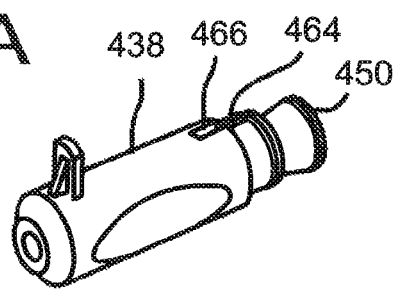
Figure 6C:
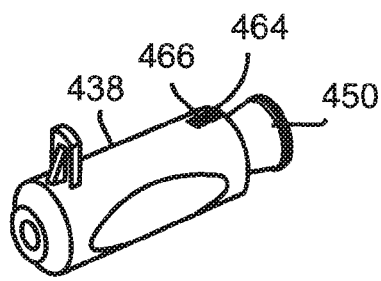

Referring to FIGS. 6A-6C, in some examples, a transseptal needle assembly 430 includes a rotatable collar 464. In some examples, the transseptal needle assembly 430 includes a distal handle 438 with a slit 466 or other opening and a proximal handle 450 with a rotatable collar 464. The proximal handle 450, in some examples, fits into the distal handle 438. In some examples, the proximal handle 450 is slidable with respect to the distal handle 438. In some examples, the rotatable collar 464 can be permanently attached to proximal handle 450. In some examples, in a first position (FIG. 6A), the rotatable collar 464 is offset from or otherwise not aligned with the slit 466 of the distal handle 438. Such a configuration, in some examples, inhibits the proximal handle 450 from sliding forward with respect to the distal handle 438. In a second position (FIG. 6B), in some examples, the rotatable collar 464 is aligned with the slit 466 of the distal handle 438. Such a configuration, in some examples, allows the proximal handle 450 to slide forward with respect to the distal handle 438, as shown in FIG. 6C, for instance, to extend an inner cannula from within an outer cannula to effect a puncture of a tissue layer.

Figure 7:
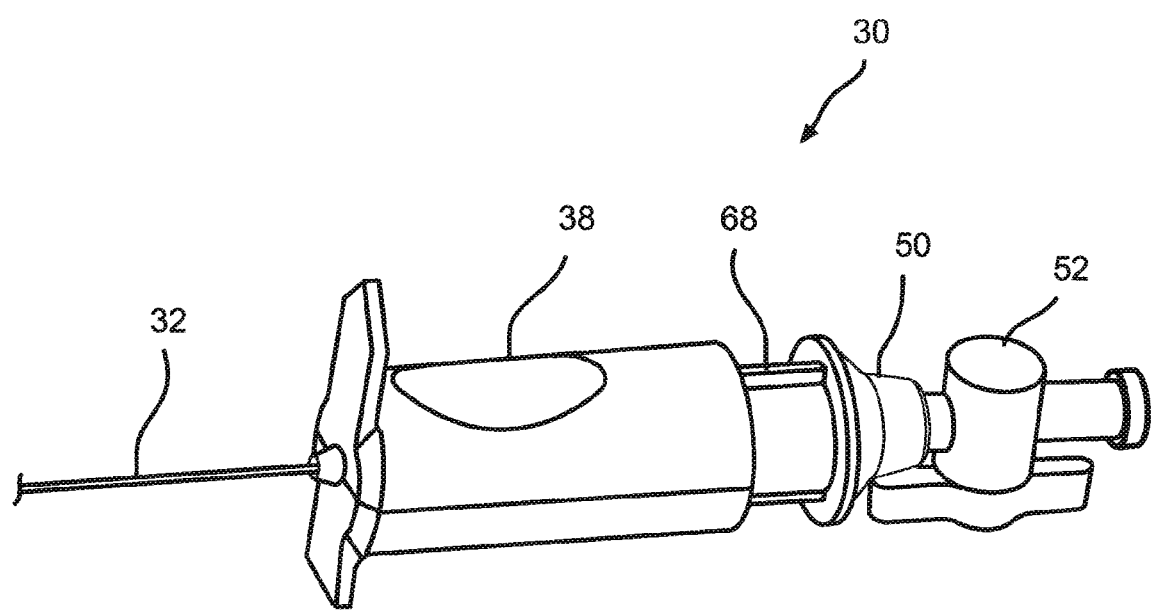
FIG. 7 is a perspective view of a needle assembly in accordance with at least one example of the invention.

Referring to FIG. 7, in some examples, a transseptal needle assembly 30 includes an outer cannula 32, a distal handle 38, a proximal handle 50 with a feature 68, and a stopcock 52 or other coupling assembly. In some examples, the feature 68 inhibits rotation of the proximal handle 50 in relation to the distal handle 38 during puncturing of a tissue layer, for instance, during transseptal catheterization. That is, the feature 68, in some examples, interacts with a mating channel or slot within the distal handle 38 in a manner similar to a keyed shaft or the like to inhibit rotation of the distal handle 38 with respect to the proximal handle 50. In other examples, other ways of inhibiting rotation of the distal handle 38 with respect to the proximal handle 50 are contemplated.

Figure 8:
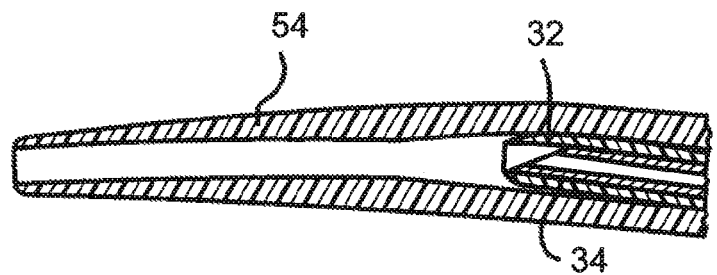
FIG. 8 is a side cross-sectional view of a dilator and an outer cannula and an inner cannula of a needle assembly in accordance with at least one example of the invention.

Referring to FIG. 8, in some examples, a dilator 54 is shown including an outer cannula 32 and an inner cannula 34 within the dilator 54. In some examples, an inner cannula 34 can be made of a metal, such as, for instance, Stainless Steel 304. In some examples, when the outer cannula 32 is inserted into the dilator 54, the inner cannula 34 is inhibited from exiting the outer cannula 32, as described herein and shown in FIG. 2. In this way, the tip of the inner cannula 34 is inhibited from scraping the dilator 54. Such scraping or skiving of the dilator 54 can, in some circumstances, generate particulate, which can be detrimental to the health of the patient. For instance, such particulate released into the patient's bloodstream can potentially lead to an adverse clinical event, such as a stroke or myocardial infarction, among other things. In some examples, the outer cannula 32 can be made of a polyethylene, such as, for instance, Petrothane. In some examples, an outer surface of the outer cannula 32 can be coated with a polymeric material, such as, but not limited to polyethylene. In further examples, a portion of the outer surface of the outer cannula 32 can be coated with a polymeric material, such as, but not limited to polyethylene. In still further examples, a distal portion of the outer surface of the outer cannula 32 can be coated with a polymeric material, such as, but not limited to polyethylene. In some examples, the tip of outer cannula 32 may be thermoformed to have a smooth, atraumatic taper. In various examples, such features of the outer cannula 32 can inhibit the outer cannula 32 from scraping the dilator 54 and generating particulate matter when the outer cannula 32 is advanced through the dilator 54, for instance.

Figure 9A:
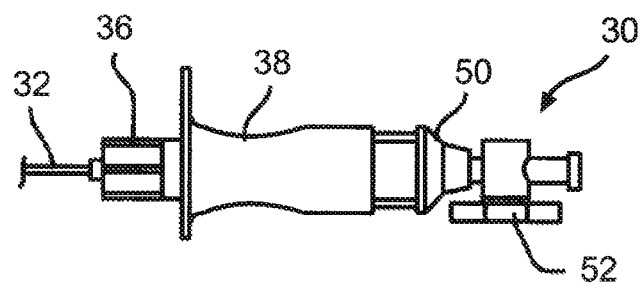
FIG. 9A is a side view of a needle assembly in accordance with at least one example of the invention, the needle assembly in a configuration in which an inner cannula is within an outer cannula.
Figure 9B:
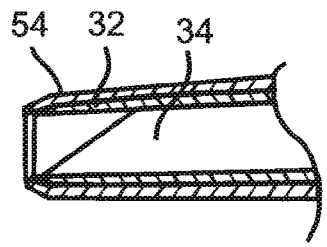
FIG. 9B is a cross-sectional side view of a tip of distal portions of the inner cannula and the outer cannula of the needle assembly of FIG. 9A.
Figure 10A:
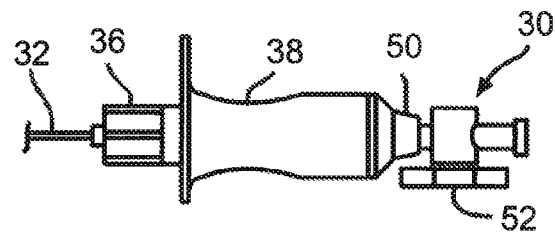
FIG. 10A is a side view of a needle assembly in accordance with at least one example of the invention, the needle assembly in a configuration in which an inner cannula is extended from an outer cannula.
Figure 10B:
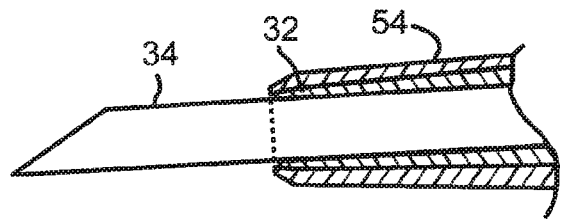
FIG. 10B is a cross-sectional side view of distal portions of the inner cannula and the outer cannula of the needle assembly of FIG. 10A.

Referring to FIGS. 9A-10B, in some examples, a transseptal needle assembly 30 includes an outer cannula 32, a rotating Luer fitting 36, a distal handle 38, a proximal handle 50, and a stopcock 52 or other coupling assembly. In some examples, the translational location of the inner cannula 34 in relation to the outer cannula 32 can be controlled by the position of the proximal handle 50 in relation to the distal handle 38. For instance, in some examples, when the proximal handle 50 is spaced from the distal handle 38, the tip of the inner cannula 34 remains withdrawn within the outer cannula 32, and the tip of the outer cannula 32 remains withdrawn within the dilator 54 (FIGS. 9A and 9B). In some examples, when the proximal handle 50 is moved forward within the distal handle 38, the inner cannula 34 exits the outer cannula 32 and the tip of the dilator 54 (FIGS. 10A and 10B). In some examples, since the inner cannula 34 can only exit the outer cannula 32 when the proximal handle 50 is moved forward within the distal handle 38, generation of particulate matter can be limited by maintaining the inner cannula 34 within the outer cannula 32 and limiting the potential for the inner cannula 34 to scrape or skive an interior of the dilator 54. Moreover, such a configuration limits potential injury to the patient due to inadvertent exposure of the patient to the inner cannula 34.

Figure 11A:
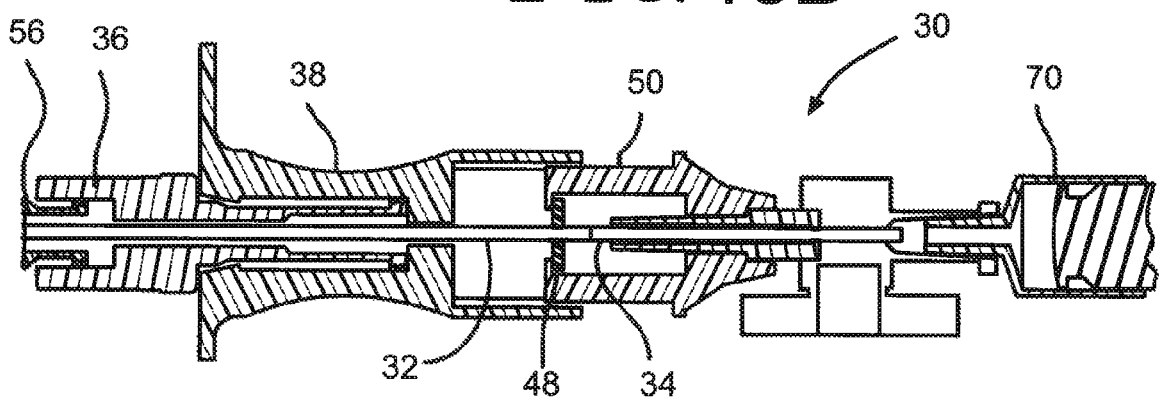
FIG. 11A is a cross-sectional view of a needle assembly in accordance with at least one example of the invention.
Figure 11B:
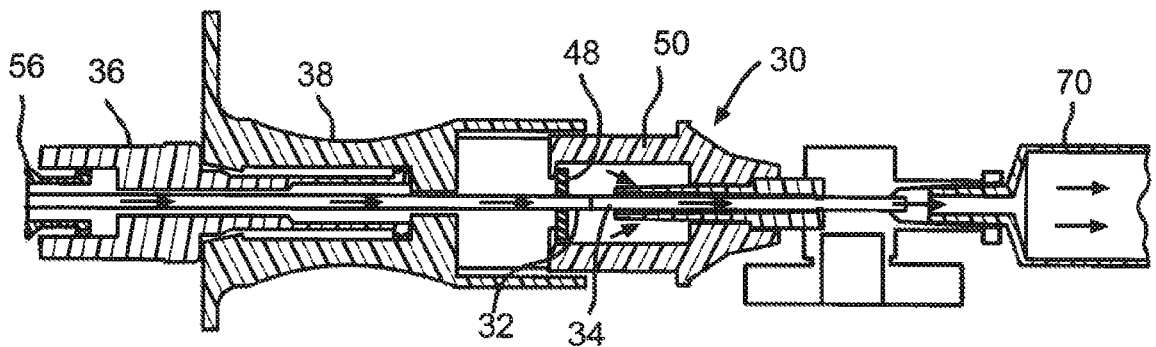
FIG. 11B is a cross-sectional view of a needle assembly in accordance with at least one example of the invention.
Figure 12:
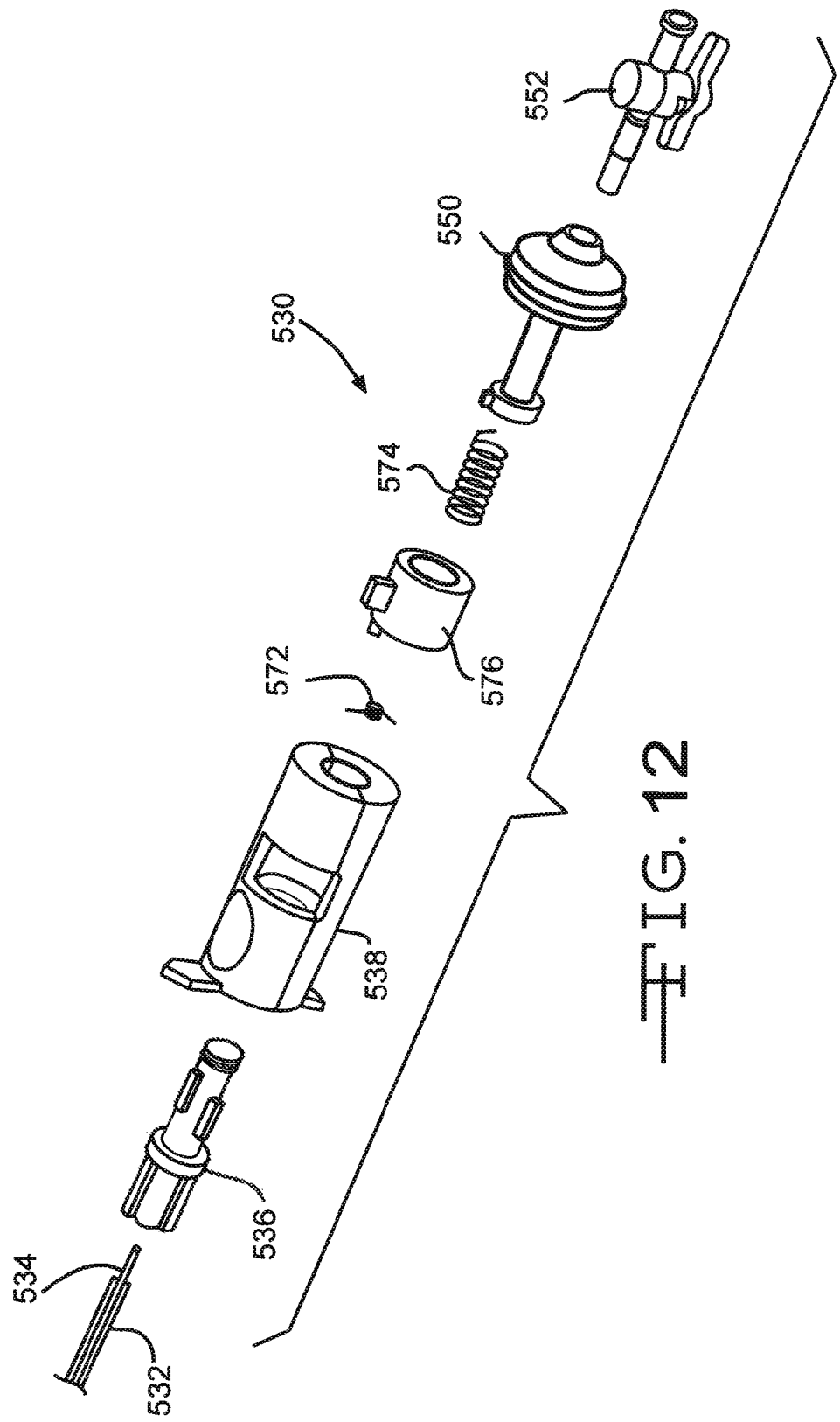
FIG. 12 is an exploded view of a needle assembly in accordance with at least one example of the invention.
Figure 13A:
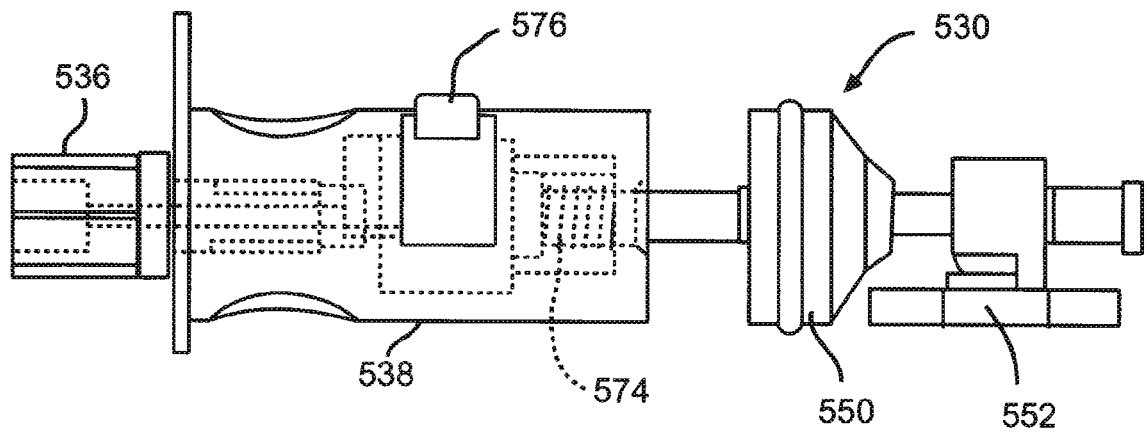
FIG. 13A is a side view of a needle assembly in accordance with at least one example of the invention, the needle assembly in a configuration in which an inner cannula is within an outer cannula.
Figure 13B:
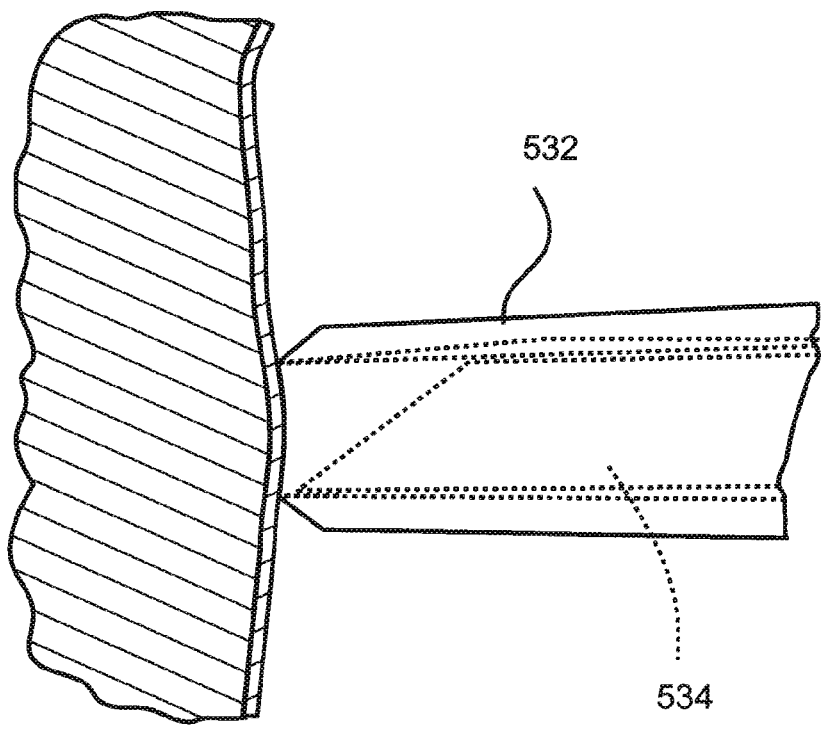
FIG. 13B is a side view of a distal portion of the needle assembly of FIG. 13A.

Referring to FIGS. 11A and 11B, in some examples, a transseptal needle assembly 30 includes an outer cannula 32, an inner cannula 34, a rotating Luer fitting 36, a distal handle 38, a hemostatic valve 48, a proximal handle 50, a stopcock 52 or other coupling assembly, a dilator hub 56, and a syringe 70. In some examples, the rotating Luer fitting 36 is fixed to the dilator hub 56, which creates a seal between the outer cannula 32 and the dilator hub 56, limiting a potential path for air to travel into the patient, for instance, into the patient's heart, which can result in the formation of an air embolism. Once this seal is created, in some examples, the physician or other user can aspirate the transseptal needle assembly 30 to remove air that could potentially generate an air embolus. In some examples, the hemostatic valve 48 is disposed within the proximal handle 50 and maintains a substantially air-tight seal around the outer cannula 32 when the proximal handle 50 moves. In this way, in some examples, aspiration removes air from the transseptal needle assembly 30 and the hemostatic valve 48 maintains a substantially air-tight floating joint between the inner cannula 32 and the outer cannula 34. After aspiration, in some examples, the physician or other user can attach the syringe 70 (for instance, filled with contrast) to the stopcock 52 or other coupling assembly in order to help in determining the location of the transseptal needle assembly 30 within the patient.

Figure 14A:
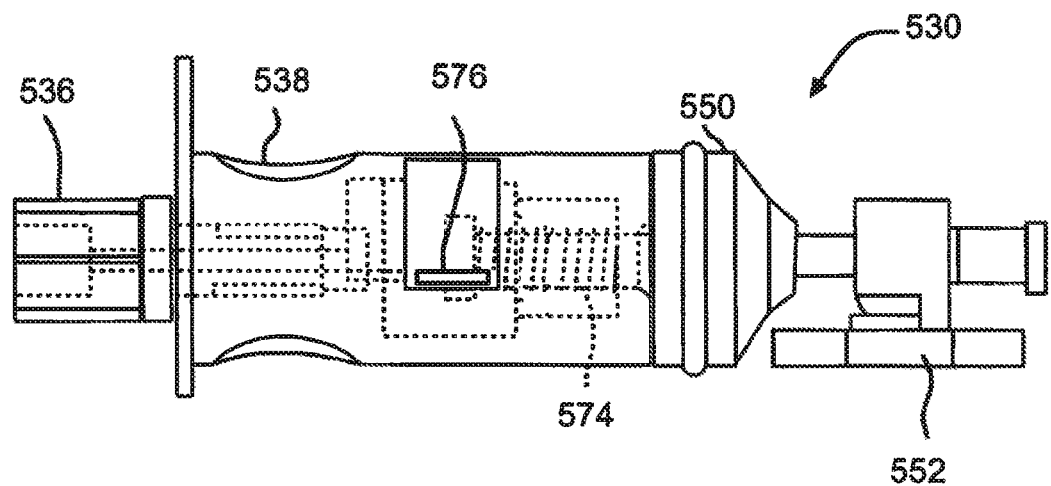
FIG. 14A is a side view of a needle assembly in accordance with at least one example of the invention, the needle assembly in a configuration in which an inner cannula is extended from an outer cannula.
Figure 14B:
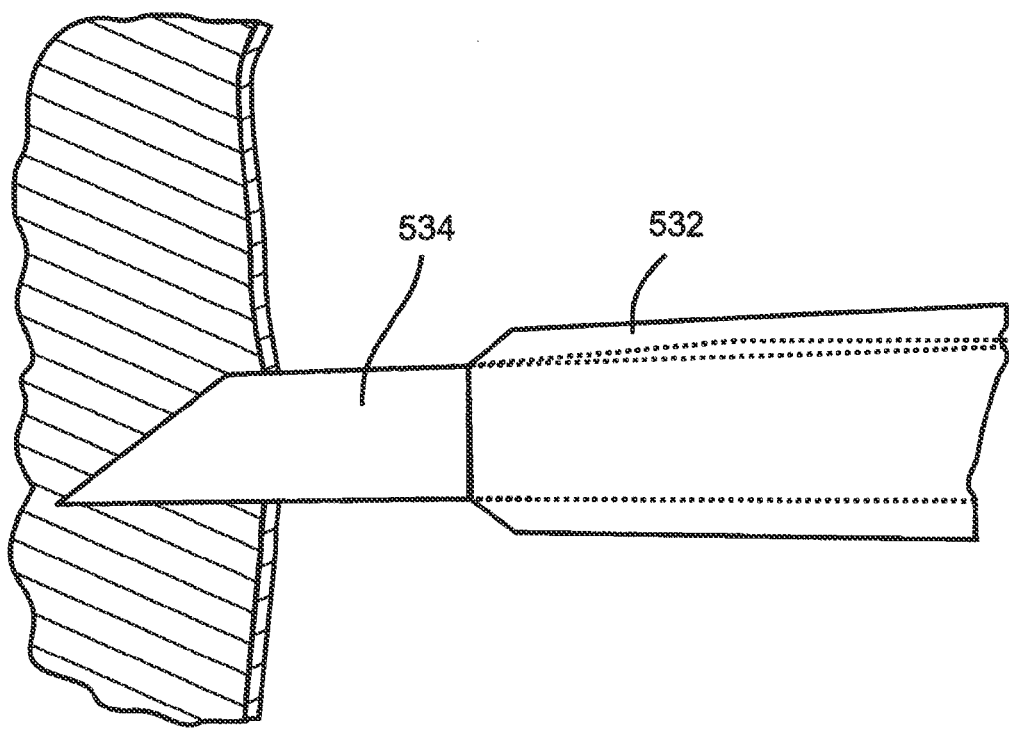
FIG. 14B is a side view of a distal portion of the needle assembly of FIG. 14A.

Referring to FIGS. 12-14B, in some examples, a transseptal needle assembly 530 includes an outer cannula 532, an inner cannula 534, a rotating Luer fitting 536, a distal handle 538, a proximal handle 550, a stopcock 552 or other coupling assembly, a torsion spring 572, a compression spring 574, and a release knob 576. In some examples, the outer cannula 532 connects to the distal handle 538. In some examples, the inner cannula 534 connects to the proximal handle 550. The inner cannula 534, in some examples, is slidable with respect to the outer cannula 532. In some examples, the proximal handle 550 fits into or onto the distal handle 538 and is slidable with respect to the distal handle 538. In some examples, the release knob 576 is connected to the torsion spring 572 to form an automatic puncture mechanism. In some examples, when the release knob 576 is not depressed, as shown in FIG. 13A, the compression spring 574 remains compressed and the proximal handle 550 is inhibited from sliding forward with respect to the distal handle 538 and, as shown in FIG. 13B, the inner cannula 534 remains retracted within outer cannula 532. In some examples, the torsion spring 572 acts to maintain the release knob 576 in the non-depressed configuration. In some examples, when the release knob 576 is depressed (for instance, overcoming the counter force created by the torsion spring 572), as shown in FIG. 14A, the compression spring 574 lengthens and acts to automatically slide proximal handle 550 forward within distal handle 538, sliding the tip of inner cannula 534 forward through outer cannula 532 to perform a puncture, as shown in FIG. 14B. When the proximal handle 550, in some examples, is pulled proximally to withdraw the inner cannula 534 back into the outer cannula 532, the torsion spring 572 causes the release knob 576 to return to the non-depressed position.

Figure 15:
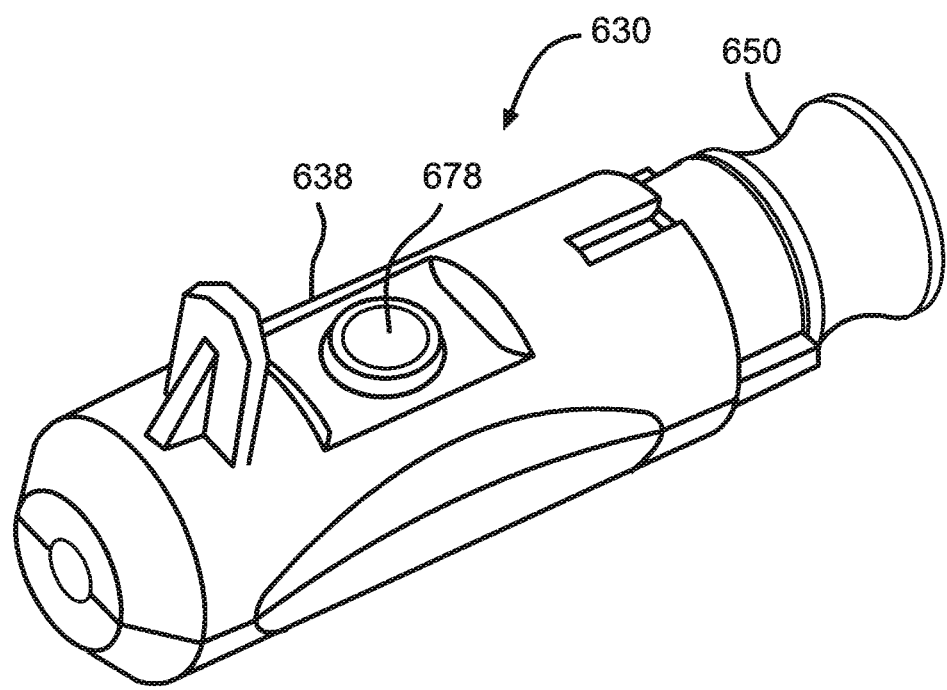
FIG. 15 is a perspective view of a needle assembly in accordance with at least one example of the invention.

Referring to FIG. 15, in some examples, a transseptal needle assembly 630 includes a release button 678. In some examples, the transseptal needle assembly 630 includes a distal handle 638, a proximal handle 650, and the release button 678. In some examples, when the release button 678 is depressed, the proximal handle 650 is automatically slid forward with respect to the distal handle 638.

Figure 16A:
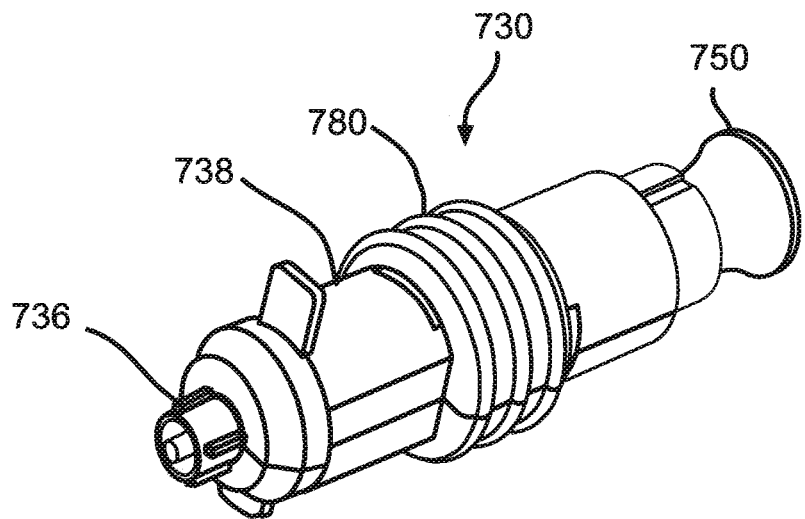
FIGS. 16A and 16B are perspective views of a needle assembly in accordance with at least one example of the invention.
Figure 16B:
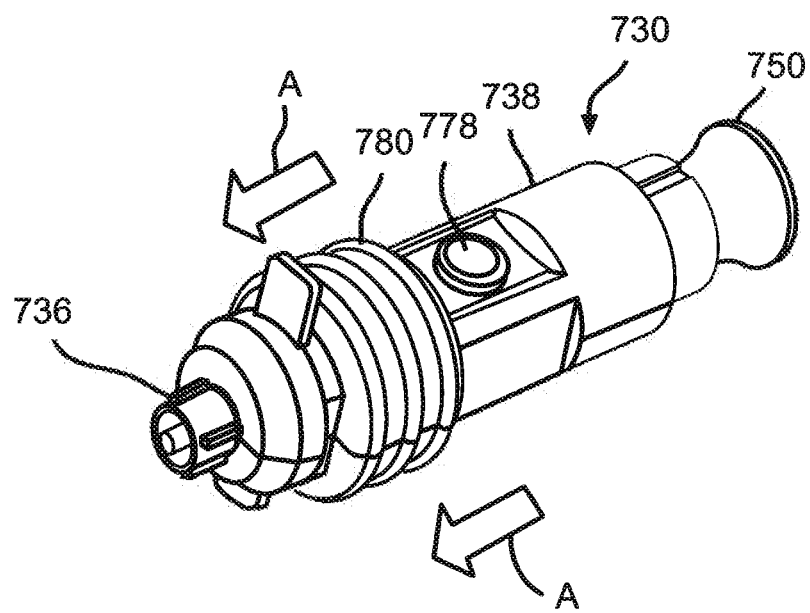

Referring to FIGS. 16A-16B, in some examples, a transseptal needle assembly 730 includes a safety mechanism, such as, but not limited to, a slidable cover 780. In some examples, a transseptal needle assembly 730 includes a rotating Luer fitting 736, a distal handle 738, a proximal handle 750, a release button 778, and a safety cover 780. In some examples, the safety cover 780 conceals the release button 778, as shown in FIG. 16A, such that the physician or other user is inhibited from accidentally triggering the automatic puncture mechanism, for instance, by accidentally depressing the release button 778. The physician or other user, in some examples, can slide the safety cover 780 forward along arrows A to expose the release button 778, as shown in FIG. 16B, for instance, when the physician or other user is ready to perform a puncture.

Referring to FIGS. 17A and 17B, a transseptal needle assembly 830, in some examples, includes a safety puncture mechanism. In some examples, the transseptal needle assembly 830 includes a rotating Luer fitting 836, a distal handle 838, a release button 878, one or more release button springs 879, a release spring 884, and a proximal handle assembly 839. In some examples, the proximal handle assembly 839 includes a lock knob 882, an outer cannula carrier 854, an inner cannula carrier 850, a resistance spring 886, an outer cannula 832, and an inner cannula 834. In some examples, the proximal handle assembly 839 is slidably connected to the distal handle 838. The outer cannula 832, in some examples, is connected to the outer cannula carrier 854. In some examples, the inner cannula 834 is connected to the inner cannula carrier 850. The lock knob 882, in some examples, rotates around the outer cannula carrier 854. The resistance spring 886, in some examples, applies a force creating an offset distance 852 between the inner cannula carrier 850 and the outer cannula carrier 854. In some examples, this offset distance 852 corresponds with a tip of the inner cannula 834 remaining within a distal tip of the outer cannula 832. As the offset distance decreases, in some examples, the inner cannula 834 moves in relation to the outer cannula 832. In various examples, at a threshold offset distance 852, the tip of the inner cannula 834 extends from the outer cannula 832. In some examples, the one or more release button springs 879 applies an upward force on the release button 878, for instance, to maintain the proximal handle assembly 839 in a locked position.

Figure 18A:
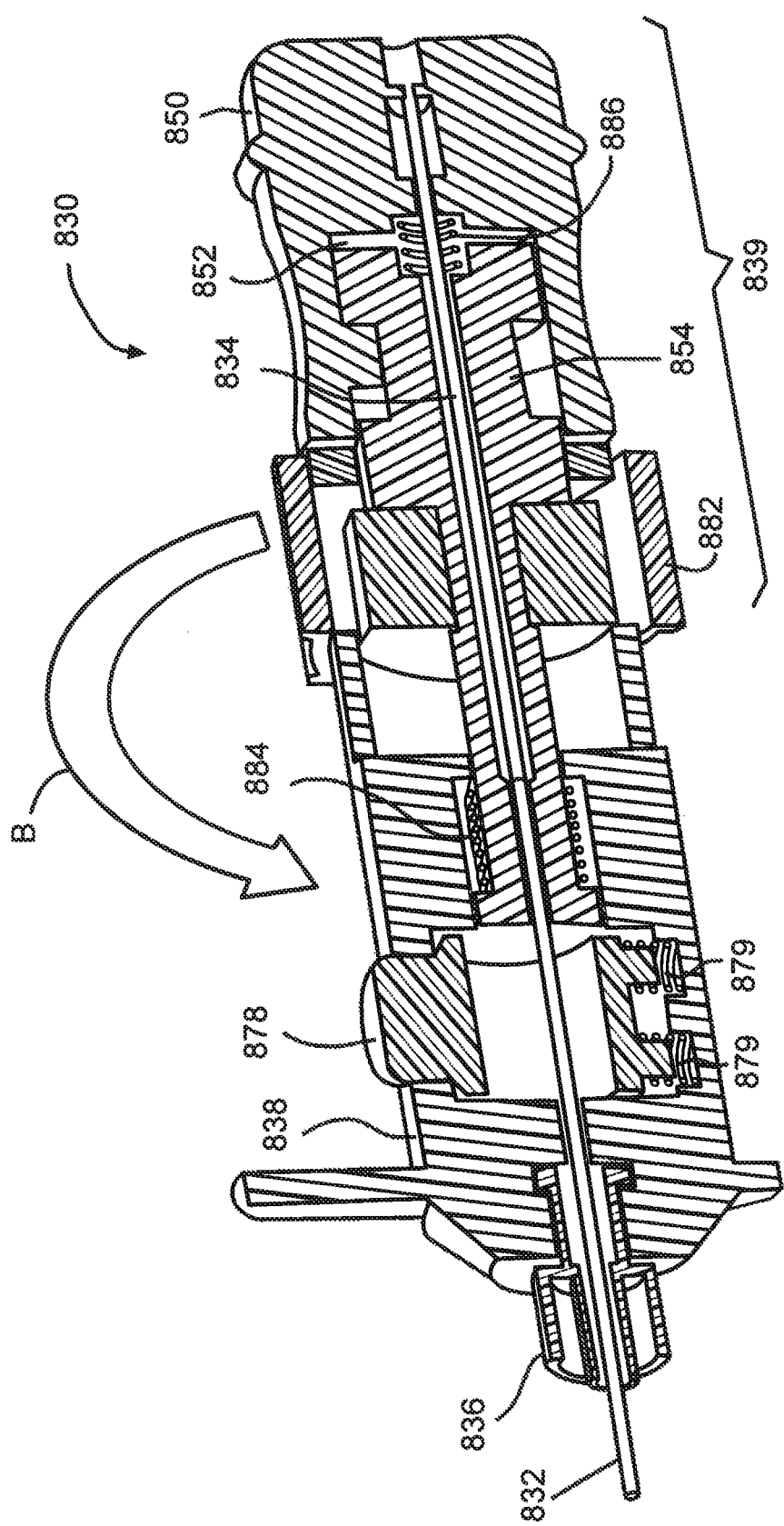
Figure 18B:
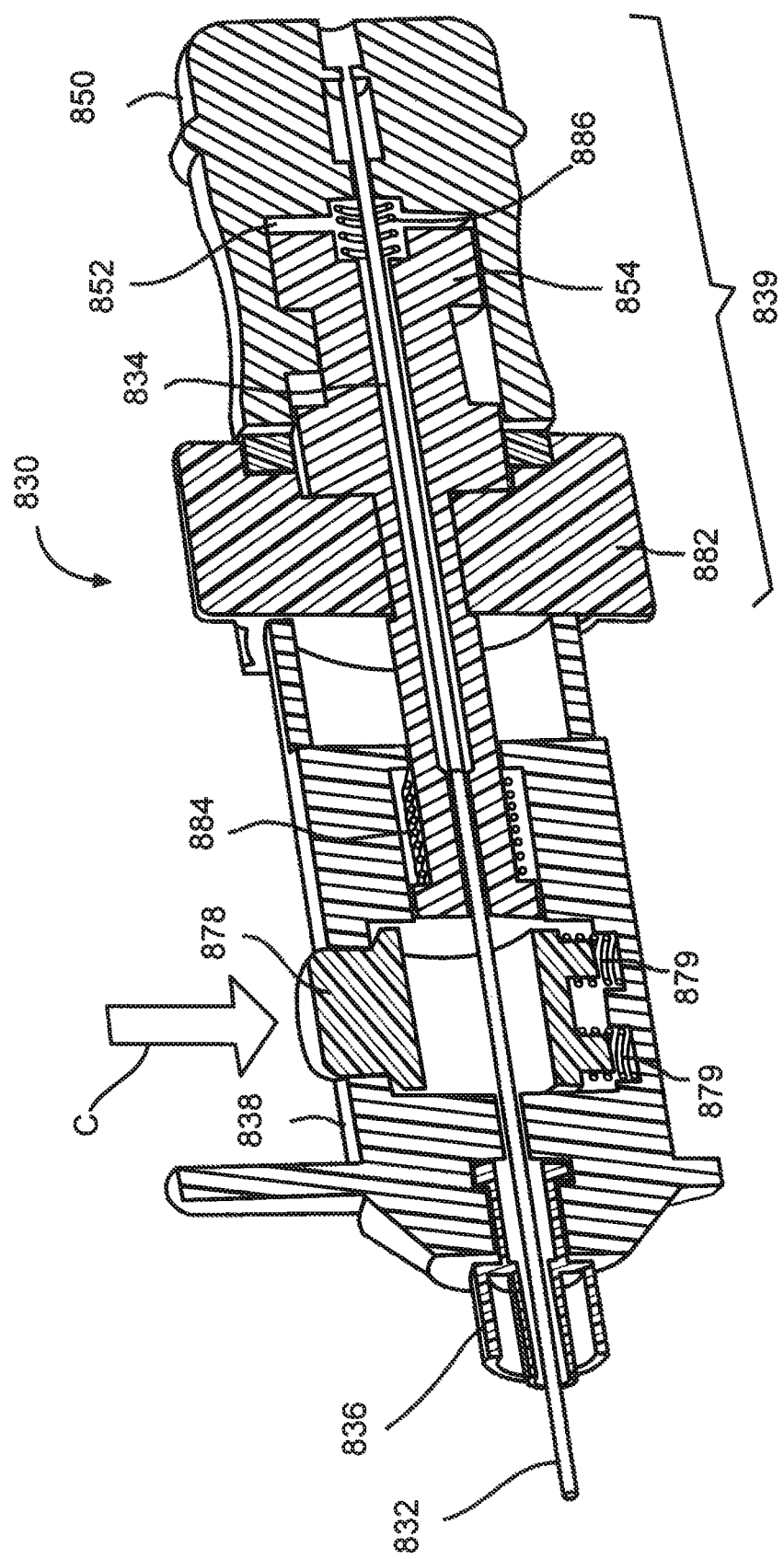
Figure 18C:
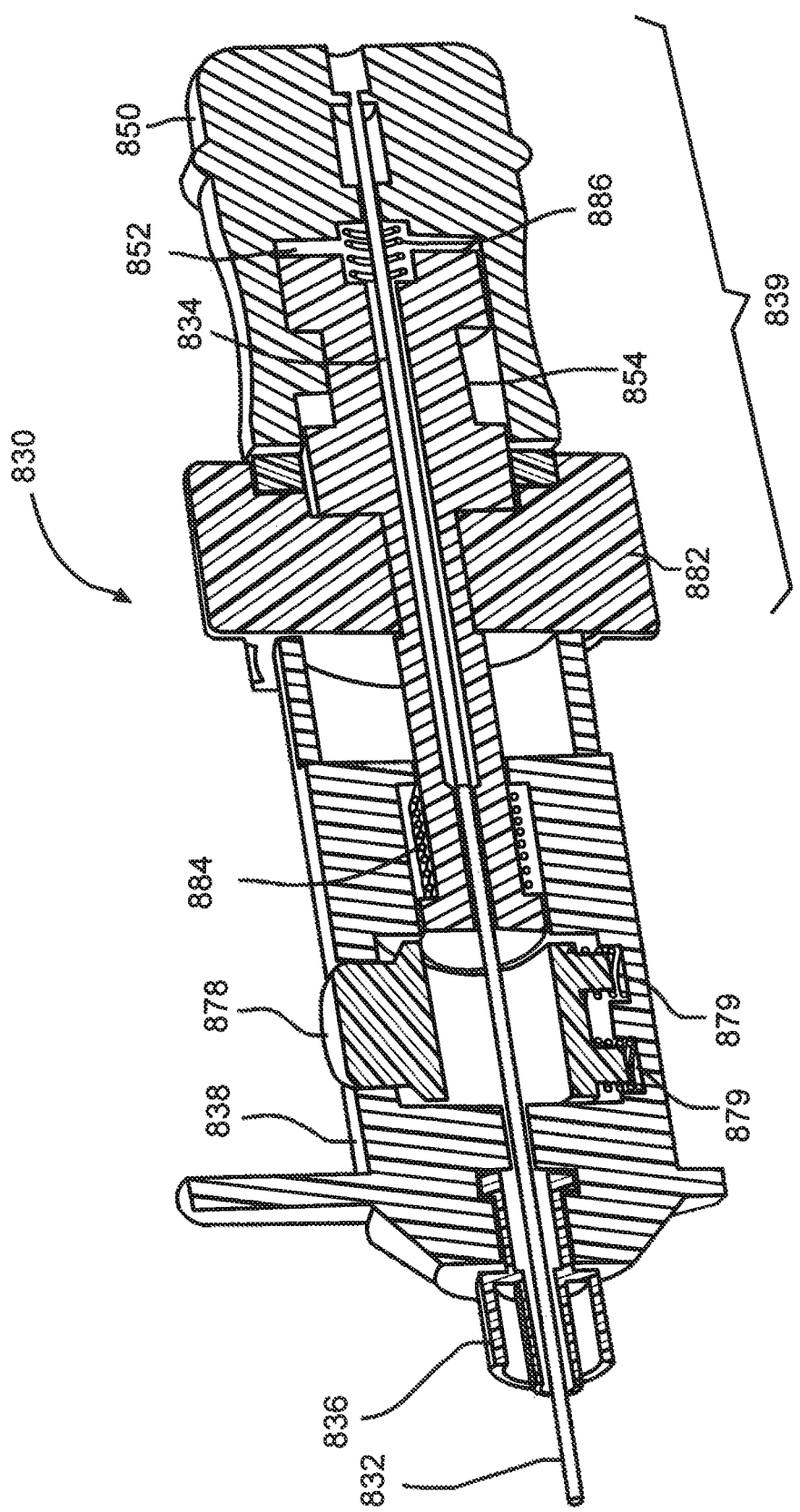
Figure 18D:
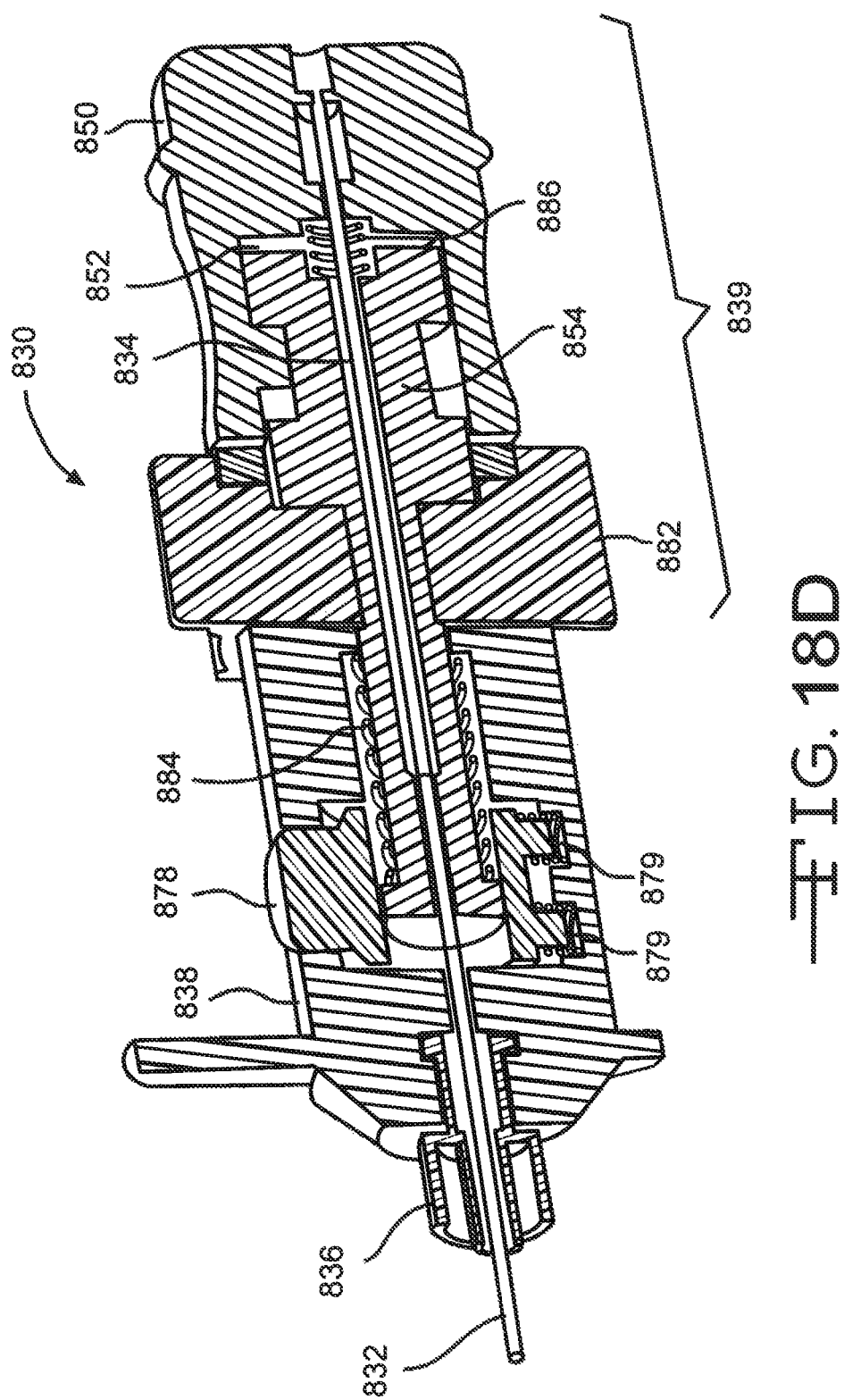
Figure 18E:
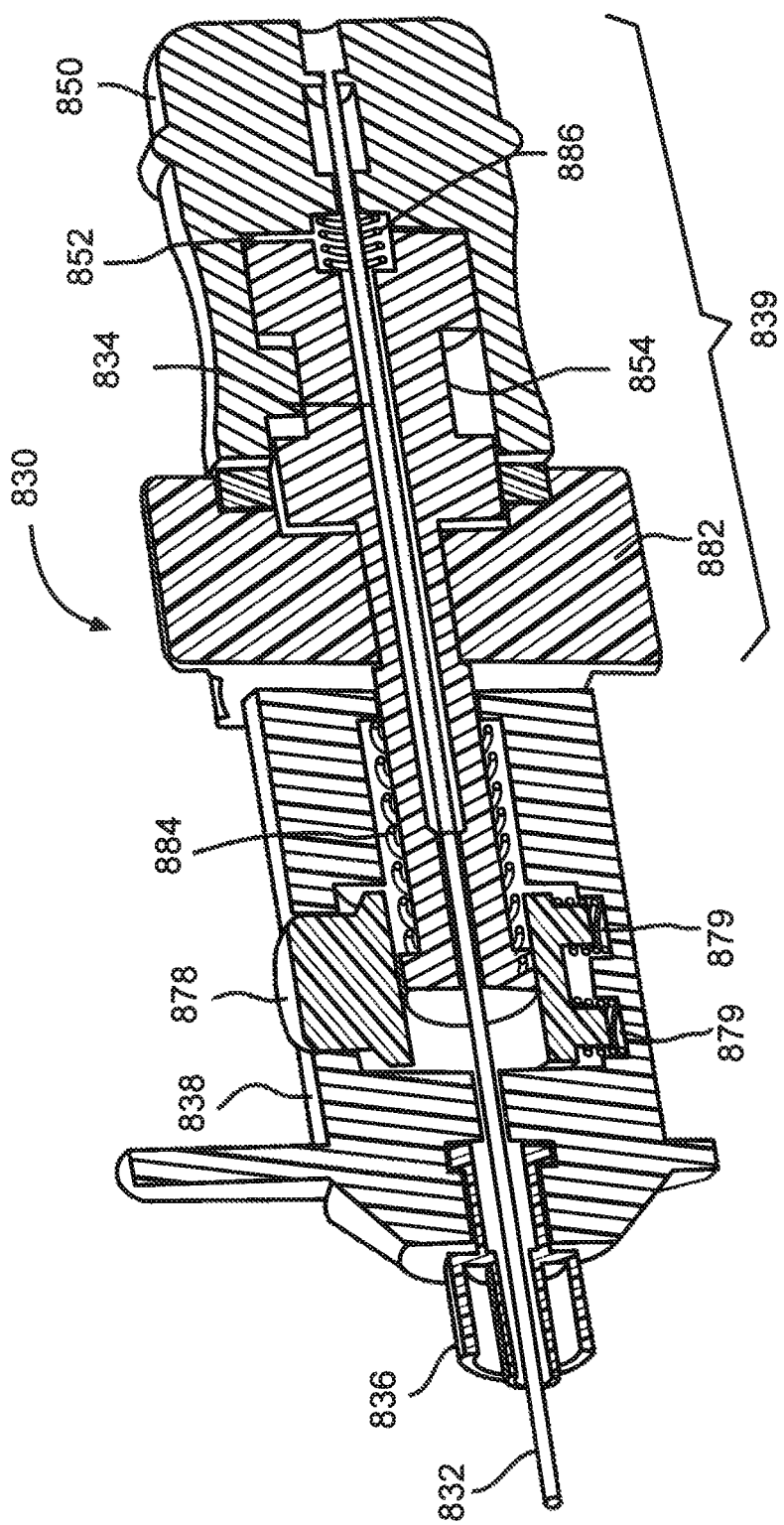
Figure 19A:
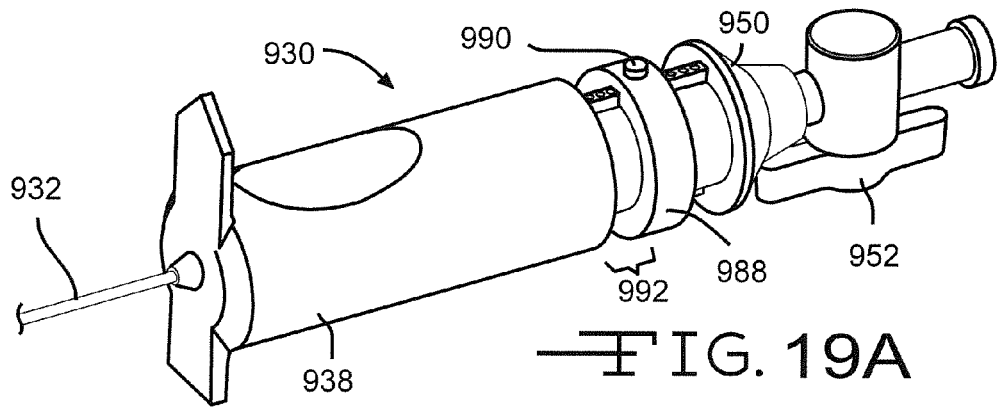
FIG. 19A is a perspective view of a needle assembly in accordance with at least one example of the invention.
Figure 19B:
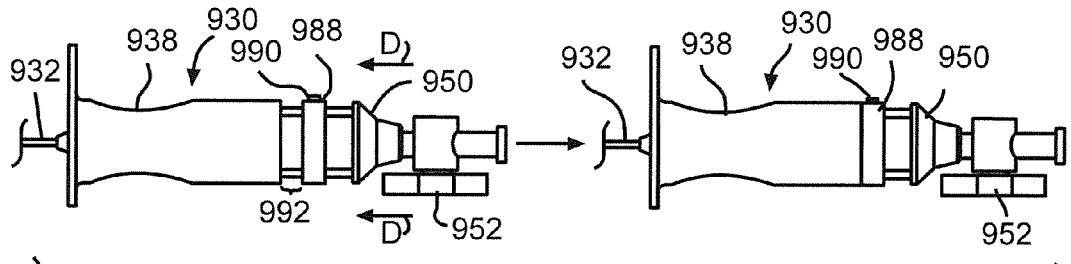
FIGS. 19B-19D are side views of the needle assembly of FIG. 19A.
Figure 19C:
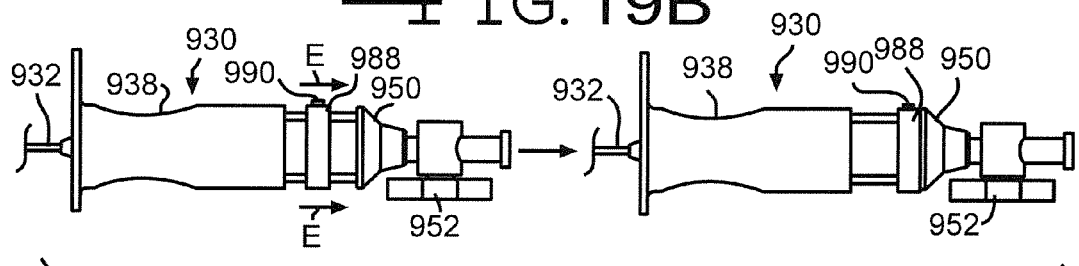
Figure 19D:
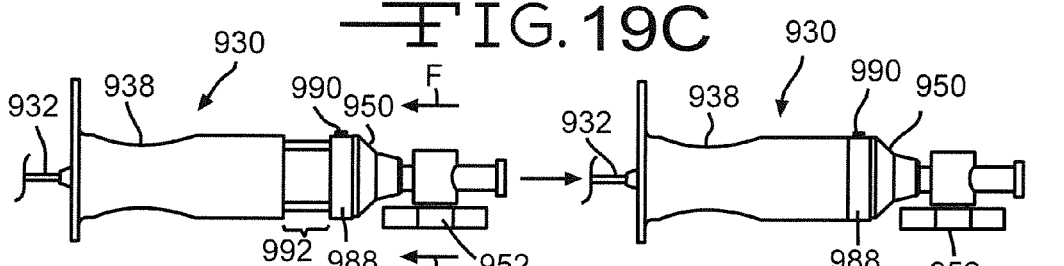

Referring now to FIGS. 17A-18F, the lock knob 882, in some examples, is rotatable to a first position and a second position. Referring to FIG. 18A, in the first position, in some examples, the lock knob 882 inhibits forward movement of the proximal handle assembly 839. In some examples, with rotation of the lock knob 882 along arrow B, the lock knob 882 can be placed in the second position. Referring to FIG. 18B, in the second position, the lock knob 882 no longer inhibits forward movement of the proximal handle assembly 839. In some examples, pushing or otherwise actuating the release button 878, for instance, along arrow C, allows the proximal handle assembly 839 to move forward with respect to the distal handle 838. Referring to FIG. 18C, in some examples, when the release button 878 is depressed, overcoming the one or more release button springs 879, the proximal handle assembly 839 is no longer inhibited from moving forward. Referring to FIG. 18D, in some examples, the release spring 884 extends and moves the proximal handle assembly 839 forward. In this way, in some examples, both the outer cannula 832 and the inner cannula 834 move forward. In some examples, the inner cannula carrier 850 is maintained at the offset distance 852 from the outer cannula carrier 854 by the resistance spring 886. In some examples, such a configuration corresponds with the tip of the inner cannula 834 remaining within the tip of the outer cannula 832. In some examples, referring to FIG. 18E, the outer cannula carrier 854 and the lock knob 882 bottom out and the momentum of the inner cannula carrier 850 overcomes the resistance spring 886, causing the offset distance 852 between the outer cannula carrier 854 and the inner cannula carrier 850 to be temporarily minimized. In this way, in some examples, the tip of the inner cannula 834 exits the tip of the outer cannula 832 temporarily, for instance, to puncture a tissue layer, such as the septum. Referring to FIG. 18F, in some examples, the compression force of the resistance spring 886 counteracts the momentum of the inner cannula carrier 850 and causes the inner cannula carrier 850 to return to a larger offset distance 852 from the outer cannula carrier 854. In some examples, this corresponds with the tip of the inner cannula 834 returning to a position where the tip of the inner cannula 834 is disposed within the outer cannula 832.

Referring to FIGS. 19A-19D, in some examples, a transseptal needle assembly 930 includes an adjustable puncture spacer 988. In some examples, the transseptal needle assembly 930 includes an outer cannula 932, a distal handle 938, a proximal handle 950, a stopcock 952 or other coupling assembly, and the adjustable puncture spacer 988. In some examples, the adjustable puncture spacer 988 includes a locking button 990. In some examples, the adjustable puncture spacer 988 is slidable along proximal handle 950 to adjust a distance 992 between the distal handle 938 and the adjustable puncture spacer 988. In some examples, the locking button 990 locks the adjustable puncture spacer 988 at a desired distance 992. In some examples, the distance 992 determines a length of a puncture performed by the transseptal needle assembly 930 when the proximal handle 950 is slid forward with respect to the distal handle 938. In some examples, the physician or other user can set a desired puncture length by unlocking the adjustable puncture spacer 988 using the locking button 990, sliding the adjustable puncture spacer 988 to a desired distance 992, and locking the adjustable puncture spacer 988 using locking button 990. For instance, in some examples, referring to FIG. 19B, a relatively short puncture distance 992 can be set to allow the proximal handle 950 to slide forward with respect to the distal handle 938 a relatively short distance along arrows D. In some examples, referring to FIG. 19C, a relatively long puncture distance 992 can be set by moving the adjustable puncture spacer 988 proximally along arrows E. With the adjustable puncture spacer 988 set in this way, in some examples, referring to FIG. 19D, the proximal handle 950 can slide forward with respect to the distal handle 938 a relatively long distance along arrows F.

Figure 20A:
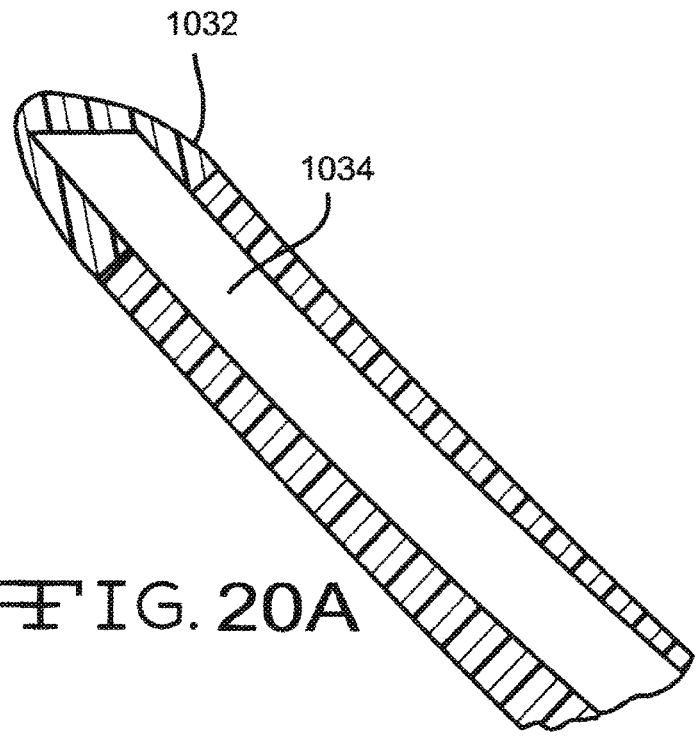
FIGS. 20A and 20B are side views of an outer cannula and an inner cannula of a needle assembly in accordance with at least one example of the invention.
Figure 20B:
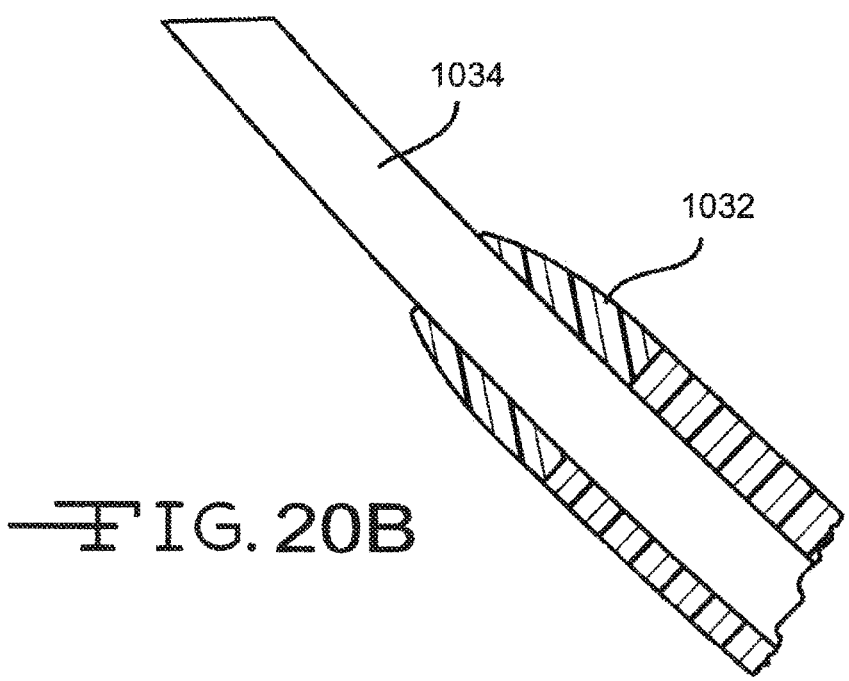

In some examples, referring to FIGS. 20A and 20B, an outer cannula 1032 includes a closed tip configured to inhibit formation of particulate with movement of the outer cannula 1032 and an inner cannula 1034 within a dilator. In some examples, the inner cannula 1034 is slidable within the outer cannula 1032. A tip of the outer cannula 1032, in some examples, is completely closed, as shown in FIG. 20A. In some examples, the tip of the outer cannula 1032 can be thermoformed to a closed configuration. In some examples, the outer cannula 1032 can be made of a polyethylene, such as, for instance, Petrothane. In some examples, the inner cannula 1034 can be made of a metal, such as, for instance, Stainless Steel 304. In some examples, the closed tip of the outer cannula 1032 shields the tip of the inner cannula 1034 and guards against scraping or skiving of an interior of the dilator, for instance, to inhibit particulate formation with movement of the inner cannula 1034 and the outer cannula 1032 through the dilator. When the inner cannula 1034 is advanced through the outer cannula 1032, in some examples, the tip of the inner cannula 1034 pierces the closed tip of the outer cannula 1032 to puncture a tissue layer, such as, for instance, a patient's fossa ovalis.

Referring now to FIGS. 1-20B, various examples are described. In some examples, an apparatus 30, 130, 530, 630, 730, 830, 930 includes a needle assembly. In some examples, the needle assembly includes an outer cannula 32, 532, 832, 932, 1032 and an inner cannula 34, 534, 834, 1034. In some examples, the outer cannula 32, 532, 832, 932, 1032 includes a tubular sidewall disposed around a lumen, at least a portion of the sidewall including an exterior including a polymeric material configured to inhibit skiving of an interior of a dilator with movement of the outer cannula within the dilator. In some examples, the inner cannula 34, 534, 834, 1034 is disposed within the lumen and is selectively slidable with respect to the outer cannula 32, 532, 832, 932, 1032. In some examples, a handle is disposed at a proximal portion of the needle assembly. In some examples, the handle includes a first handle portion 38, 138, 438, 538, 638, 854, 938 coupled to and movable with the outer cannula 32, 532, 832, 932, 1032. In some examples, a second handle portion 50, 150, 450, 550, 650, 750, 850, 950 is coupled to and movable with the inner cannula 34, 534, 834, 1034. In some examples, the first handle portion 38, 138, 438, 538, 638, 854, 938 is selectively movable with respect to the second handle portion 50, 150, 450, 550, 650, 750, 850, 950 to extend a distal end of the inner cannula 34, 534, 834, 1034 from within the lumen of the outer cannula 32, 532, 832, 932, 1032. In some examples, the outer cannula 32, 532, 832, 932, 1032 is formed from the polymeric material. In some examples, the outer cannula 32, 532, 832, 932, 1032 is formed from polyethylene. In some examples, the outer cannula 32, 532, 832, 932, 1032 is formed from Petrothane.

In some examples, the apparatus 30, 130, 530, 630, 730, 830, 930 includes a handle lock 40, 44, 140, 144, 240, 244, 340, 344, 464, 466, 576, 882 includes a first position in which the handle lock 40, 44, 140, 144, 240, 244, 340, 344, 464, 466, 576, 882 inhibits movement of the second handle portion 50, 150, 450, 550, 650, 750, 850, 950 with respect to the first handle portion 38, 138, 438, 538, 638, 854, 938 and a second position in which the handle lock 40, 44, 140, 144, 240, 244, 340, 344, 464, 466, 576, 882 allows movement of the second handle portion 50, 150, 450, 550, 650, 750, 850, 950 with respect to the first handle portion 38, 138, 438, 538, 638, 854, 938. In some examples, the handle lock 40, 44, 140, 144, 240, 244, 340, 344, 464, 466, 576, 882 includes a spacer 40, 44, 140, 144, 240, 244, 340, 344 removably disposed with respect to the handle, wherein the spacer 40, 44, 140, 144, 240, 244, 340, 344 in the first position includes the spacer 40, 44, 140, 144, 240, 244, 340, 344 engaged with the handle to inhibit movement of the second handle portion 50, 150, 450, 550, 650, 750, 850, 950 with respect to the first handle portion 38, 138, 438, 538, 638, 854, 938, and the spacer 40, 44, 140, 144, 240, 244, 340, 344 in the second position includes the spacer 40, 44, 140, 144, 240, 244, 340, 344 removed from engagement with the handle to allow movement of the second handle portion 50, 150, 450, 550, 650, 750, 850, 950 with respect to the first handle portion 38, 138, 438, 538, 638, 854, 938 to allow movement of the inner cannula 34, 534, 834, 1034 with respect to the outer cannula 32, 532, 832, 932, 1032. In some examples, the handle lock 40, 44, 140, 144, 240, 244, 340, 344, 464, 466, 576, 882 includes a movable lock 464, 466, 576, 882 associated with the handle, wherein the movable lock 464, 466, 576, 882 in the first position includes the movable lock 464, 466, 576, 882 disposed with respect to the handle to inhibit movement of the second handle portion 50, 150, 450, 550, 650, 750, 850, 950 with respect to the first handle portion 38, 138, 438, 538, 638, 854, 938, and the movable lock 464, 466, 576, 882 in the second position includes the movable lock 464, 466, 576, 882 disposed with respect to the handle to allow movement of the second handle portion 50, 150, 450, 550, 650, 750, 850, 950 with respect to the first handle portion 38, 138, 438, 538, 638, 854, 938 to allow movement of the inner cannula 34, 534, 834, 1034 with respect to the outer cannula 32, 532, 832, 932, 1032. In some examples, the movable lock 464, 466, 576, 882 includes a rotational lock 464, 466, 576, 882, wherein the rotational lock 464, 466, 576, 882 in the first position includes the rotational lock 464, 466, 576, 882 in a first rotational orientation with respect to the handle, and the rotational lock 464, 466, 576, 882 in the second position includes the rotational lock 464, 466, 576, 882 in a second rotational orientation with respect to the handle. In some examples, one of the rotational lock 464, 466, 576, 882 and the handle includes a protrusion 464 and the other of the rotational lock 464, 466, 576, 882 and the handle includes a slot 466, wherein in the first rotational orientation, the slot 466 and the protrusion 464 are misaligned to inhibit movement of the second handle portion 50, 150, 450, 550, 650, 750, 850, 950 with respect to the first handle portion 38, 138, 438, 538, 638, 854, 938, and, in the second rotational orientation, the slot 466 and the protrusion 464 are aligned to allow the protrusion 464 to move within the slot 466 and allow movement of the second handle portion 50, 150, 450, 550, 650, 750, 850, 950 with respect to the first handle portion 38, 138, 438, 538, 638, 854, 938.

In some examples, the apparatus 30, 130, 530, 630, 730, 830, 930 includes a puncture assembly including a potential energy storage member 574, 884 disposed between the first handle portion 38, 138, 438, 538, 638, 854, 938 and the second handle portion 50, 150, 450, 550, 650, 750, 850, 950. In some examples, an actuator 678, 778, 878 is operatively coupled to the potential energy storage member 574, 884, wherein triggering of the actuator 678, 778, 878 releases the potential energy storage member 574, 884 to move the second handle portion 50, 150, 450, 550, 650, 750, 850, 950 with respect to the first handle portion 38, 138, 438, 538, 638, 854, 938. In some examples, the potential energy storage member 574, 884 includes a spring 574, 884. In some examples, the potential energy storage member 574, 884 includes compressed air, opposing magnets, or the like. In some examples, the distal end of the inner cannula 34, 534, 834, 1034 is biased to a position within the lumen of the outer cannula 32, 532, 832, 932, 1032, such that the distal end of the inner cannula 34, 534, 834, 1034 withdraws back into the outer cannula 32, 532, 832, 932, 1032 after a puncture is performed.

In some examples, the apparatus 30, 130, 530, 630, 730, 830, 930 includes a guard 780 movable between a locked position and an unlocked position, wherein the guard 780 in the locked position inhibits releasing of the potential energy storage member 574, 884, and the guard in the unlocked position allows releasing of the potential energy storage member 574, 884. In some examples, the guard 780 in the locked position covers the actuator 678, 778, 878, and the guard 780 in the unlocked position allows access to the actuator 678, 778, 878.

In some examples, the apparatus 30, 130, 530, 630, 730, 830, 930 includes an adjustable stop 988 associated with the handle, wherein movement of the adjustable stop 988 adjusts a distance the first handle portion 38, 138, 438, 538, 638, 854, 938 is movable with respect to the second handle portion 50, 150, 450, 550, 650, 750, 850, 950 to adjust a puncture length of the inner cannula 34, 534, 834, 1034, the puncture length including a distance the distal end of the inner cannula 34, 534, 834, 1034 extends from within the lumen of the outer cannula 32, 532, 832, 932, 1032 with movement of the first handle portion 38, 138, 438, 538, 638, 854, 938 with respect to the second handle portion 50, 150, 450, 550, 650, 750, 850, 950.

In some examples, the apparatus 30, 130, 530, 630, 730, 830, 930 includes an outer cannula cover 1032 which covers over a distal opening of the outer cannula 32, 532, 832, 932, 1032. In some examples, the outer cannula cover 1032 is puncturable by the inner cannula 34, 534, 834, 1034 with extension of the distal end of the inner cannula 34, 534, 834, 1034 from within the lumen and out of the distal opening of the outer cannula 32, 532, 832, 932, 1032. In some examples, as shown in FIG. 20A, the outer cannula cover 1032 includes a frangible distal end to cover over the distal opening of the outer cannula 32, 532, 832, 932, 1032. The frangible distal end, in some examples, is configured to puncture, break, rip, or otherwise open with extension of the inner cannula 34, 534, 834, 1034 through the outer cannula cover 1032, as shown in FIG. 20B. That is, in some examples, a non-resealable opening is formed in the outer cannula cover 1032 with extension of the sharpened tip of the inner cannula 34, 534, 834, 1034 through the outer cannula cover 1032.

The present inventors have recognized various advantages of the subject matter described herein. For instance, in some examples, the present subject matter can be used to decrease the likelihood that the needle assembly will produce particulate matter, for instance, during insertion of the needle assembly into a dilator. In various examples, the needle assembly of the present subject matter can also decrease the need for a stylet and allows a tip of an inner cannula to be sharper than most conventional transseptal needles, since the tip of the inner cannula remains housed within the outer cannula until a physician or other user is ready to perform a puncture. Additionally, the sharper tip of the inner cannula, in some examples, can allow the physician or other user to puncture an aneurismal septum or a fibrotic septum where a conventional transseptal needle would be ineffective to puncture such an aneurismal septum or fibrotic septum. In various examples, the present subject matter can decrease the risk of inadvertent exposure of the inner cannula tip, as well as decrease the need for ex vivo measurement steps typically performed to guard against inadvertent exposure. In some examples, the needle assembly of the present subject matter can decrease the likelihood of air emboli generation that can occur during puncture of a tissue layer. While various advantages of the example needle assemblies are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus comprising:
   a needle assembly including:
   an outer cannula including a tubular sidewall disposed around a lumen, at least a portion of the sidewall including an exterior including a polymeric material configured to inhibit skiving of an interior of a dilator with movement of the outer cannula within the dilator;
   an inner cannula disposed within the lumen and selectively slidable with respect to the outer cannula, the inner cannula including a distal end including a sharpened tip, wherein the sharpened tip of the inner cannula remains disposed within the outer cannula during insertion of the needle assembly within the dilator to protect the interior of the dilator from the sharpened tip and inhibit skiving of the interior of the dilator by the sharpened tip; and
   an outer cannula cover extending distally from the outer cannula to cover over and completely close off a distal opening of the outer cannula and to shield the sharpened tip of the inner cannula to further guard against skiving of the interior of the dilator by the sharpened tip, wherein the outer cannula cover includes a frangible distal end, such that a non-resealable opening is formed in the outer cannula cover with extension of the sharpened tip of the inner cannula through the outer cannula cover; and
   a handle disposed at a proximal portion of the needle assembly, the handle including:
   a first handle portion coupled to and movable with the outer cannula; and
   a second handle portion coupled to and movable with the inner cannula, wherein the first handle portion is selectively movable with respect to the second handle portion to extend the sharpened tip of the inner cannula outwardly from within the lumen of the outer cannula.

2. The apparatus of claim 1, wherein the outer cannula is formed from the polymeric material.

3. The apparatus of claim 1, wherein the outer cannula is formed from polyethylene.

4. The apparatus of claim 3, wherein the outer cannula is formed from Petrothane.

5. The apparatus of claim 1, comprising a handle lock including a first position in which the handle lock inhibits movement of the second handle portion with respect to the first handle portion and a second position in which the handle lock allows movement of the second handle portion with respect to the first handle portion.

6. The apparatus of claim 5, wherein the handle lock includes a spacer removably disposed with respect to the handle, wherein the spacer in the first position includes the spacer engaged with the handle to inhibit movement of the second handle portion with respect to the first handle portion, and the spacer in the second position includes the spacer removed from engagement with the handle to allow movement of the second handle portion with respect to the first handle portion to allow movement of the inner cannula with respect to the outer cannula.

7. The apparatus of claim 5, wherein the handle lock includes a movable lock associated with the handle, wherein the movable lock in the first position includes the movable lock disposed with respect to the handle to inhibit movement of the second handle portion with respect to the first handle portion, and the movable lock in the second position includes the movable lock disposed with respect to the handle to allow movement of the second handle portion with respect to the first handle portion to allow movement of the inner cannula with respect to the outer cannula.

8. The apparatus of claim 7, wherein the movable lock includes a rotational lock, wherein the rotational lock in the first position includes the rotational lock in a first rotational orientation with respect to the handle, and the rotational lock in the second position includes the rotational lock in a second rotational orientation with respect to the handle.

9. The apparatus of claim 8, wherein one of the rotational lock and the handle includes a protrusion and the other of the rotational lock and the handle includes a slot, wherein in the first rotational orientation, the slot and the protrusion are misaligned to inhibit movement of the second handle portion with respect to the first handle portion, and, in the second rotational orientation, the slot and the protrusion are aligned to allow the protrusion to move within the slot and allow movement of the second handle portion with respect to the first handle portion.

10. The apparatus of claim 1, comprising a puncture assembly including:
    a potential energy storage member disposed between the first handle portion and the second handle portion; and
    an actuator operatively coupled to the potential energy storage member, wherein triggering of the actuator releases the potential energy storage member to move the second handle portion with respect to the first handle portion.

11. The apparatus of claim 10, wherein the potential energy storage member includes a spring.

12. The apparatus of claim 10, comprising a guard movable between a locked position and an unlocked position, wherein the guard in the locked position inhibits releasing of the potential energy storage member, and the guard in the unlocked position allows releasing of the potential energy storage member.

13. The apparatus of claim 12, wherein the guard in the locked position covers the actuator, and the guard in the unlocked position allows access to the actuator.

14. The apparatus of claim 1, comprising an adjustable stop associated with the handle, wherein movement of the adjustable stop adjusts a distance the first handle portion is movable with respect to the second handle portion to adjust a puncture length of the inner cannula, the puncture length including a distance the distal end of the inner cannula extends from within the lumen of the outer cannula with movement of the first handle portion with respect to the second handle portion.

15. The apparatus of claim 1, wherein the outer cannula cover is puncturable by the inner cannula with extension of the distal end of the inner cannula from within the lumen and out of the distal opening of the outer cannula.

16. The apparatus of claim 1, wherein the distal end of the inner cannula is biased to a position within the lumen of the outer cannula, such that the distal end of the inner cannula withdraws back into the outer cannula after a puncture is performed.

17. The apparatus of claim 1, wherein the sharpened tip of the inner cannula is configured to remain housed within the outer cannula except when the sharpened tip is extended from within the lumen of the outer cannula to puncture the outer cannula cover and perform a puncture of a septum.

18. An apparatus comprising:
a needle assembly including:
- an outer cannula including a tubular sidewall disposed around a lumen, at least a portion of the sidewall including an exterior including a polymeric material configured to inhibit skiving of an interior of a dilator with movement of the outer cannula within the dilator;
- an inner cannula disposed within the lumen and selectively slidable with respect to the outer cannula, the inner cannula including a distal end including a sharpened tip, wherein the sharpened tip of the inner cannula remains disposed within the outer cannula during insertion of the needle assembly within the dilator to protect the interior of the dilator from the sharpened tip and inhibit skiving of the interior of the dilator by the sharpened tip; and
- an outer cannula cover extending distally from the outer cannula to cover over and completely close off a distal opening of the outer cannula and to shield the sharpened tip of the inner cannula to further guard against skiving of the interior of the dilator by the sharpened tip, wherein the outer cannula cover includes a frangible distal end, such that a non-resealable opening is formed in the outer cannula cover with extension of the sharpened tip of the inner cannula through the outer cannula cover;

a handle disposed at a proximal portion of the needle assembly, the handle including:
- a first handle portion coupled to and movable with the outer cannula; and
- a second handle portion coupled to and movable with the inner cannula, wherein the first handle portion is selectively movable with respect to the second handle portion to extend the sharpened tip of the inner cannula outwardly from within the lumen of the outer cannula, wherein the outer cannula cover is puncturable by the sharpened tip of the inner cannula with extension of the distal end of the inner cannula from within the lumen and out of the distal opening of the outer cannula; and
- a handle lock including a first position in which the handle lock inhibits movement of the second handle portion with respect to the first handle portion and a second position in which the handle lock allows movement of the second handle portion with respect to the first handle portion.

19. The apparatus of claim 18, wherein the outer cannula is formed entirely from the polymeric material.

20. The apparatus of claim 18, wherein the handle lock includes a spacer removably disposed with respect to the handle, wherein the spacer in the first position includes the spacer engaged with the handle to inhibit movement of the second handle portion with respect to the first handle portion, and the spacer in the second position includes the spacer removed from engagement with the handle to allow movement of the second handle portion with respect to the first handle portion to allow movement of the inner cannula with respect to the outer cannula.

21. The apparatus of claim 18, comprising a puncture assembly including:
- a potential energy storage member disposed between the first handle portion and the second handle portion; and
- an actuator operatively coupled to the potential energy storage member, wherein triggering of the actuator releases the potential energy storage member to move the second handle portion with respect to the first handle portion.

22. The apparatus of claim 18, wherein the sharpened tip of the inner cannula is configured to remain housed within the outer cannula except when the sharpened tip is extended from within the lumen of the outer cannula to puncture the outer cannula cover and perform a puncture of a septum.

* * * * *